United States Patent
Su et al.

(10) Patent No.: US 10,752,621 B2
(45) Date of Patent: Aug. 25, 2020

(54) OXAZOLIDINONE COMPOUNDS AND METHODS OF USE THEREOF AS ANTIBACTERIAL AGENTS

(71) Applicant: Merck Sharp & Dohme Corp., Rahway, NJ (US)

(72) Inventors: Jing Su, Scotch Plains, NJ (US); Lihu Yang, Edison, NJ (US); Takao Suzuki, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/490,958

(22) PCT Filed: Mar. 15, 2018

(86) PCT No.: PCT/US2018/022531
§ 371 (c)(1),
(2) Date: Sep. 4, 2019

(87) PCT Pub. No.: WO2018/175185
PCT Pub. Date: Sep. 27, 2018

(65) Prior Publication Data
US 2020/0010463 A1 Jan. 9, 2020

(30) Foreign Application Priority Data

Mar. 20, 2017 (CN) .............. PCT/CN2017/077256

(51) Int. Cl.
| | | |
|---|---|---|
| C07D 413/14 | (2006.01) | |
| C07D 263/22 | (2006.01) | |
| C07D 413/10 | (2006.01) | |
| C07D 417/14 | (2006.01) | |
| A61P 31/06 | (2006.01) | |
| A61K 9/00 | (2006.01) | |

(52) U.S. Cl.
CPC .......... *C07D 413/14* (2013.01); *A61K 9/0014* (2013.01); *A61K 9/0019* (2013.01); *A61K 9/0053* (2013.01); *A61P 31/06* (2018.01); *C07D 263/22* (2013.01); *C07D 413/10* (2013.01); *C07D 417/14* (2013.01)

(58) Field of Classification Search
CPC .. C07D 413/14; C07D 413/10; C07D 417/14; C07D 263/22
See application file for complete search history.

(56) References Cited

U.S. PATENT DOCUMENTS

| | | | |
|---|---|---|---|
| 5,792,765 A | 8/1998 | Riedl et al. | |
| 5,922,708 A | 7/1999 | Riedl et al. | |

FOREIGN PATENT DOCUMENTS

| | | | |
|---|---|---|---|
| DE | 19604223 A1 | 8/1997 | |
| WO | WO2001042229 A1 | 6/2001 | |
| WO | WO2004009587 A1 | 1/2004 | |
| WO | WO2005003087 A2 | 1/2005 | |
| WO | 2017058691 A1 | 4/2017 | |

OTHER PUBLICATIONS

Tokuyama et al. Chem. Pharm. Bull. 49(4) 347-352 (2001).*
Brown, Ashley et al., Relationship Between Linezolid (LZD) Exposure Profiles and Toxicity in the Hollow Fiber Infection Model (HFIM) System, Institute for Therapeutic Innovation, University of Florida, 2014, 54th Interscience Conference of Antimicrobial Agents and Chemotherapy (ICAAC) Poster, A-026b.
Flanagan, Shawn, et al., Nonclinical and Pharmacokinetic Assessments to Evaluate the Potential of Tedizolid and Linezolid to Affect Mitochondrial Function, Antimicrobial Agents and Chemotherapy, 2015, p. 178-185, vol. 59, No. 1.
Guo, Bin, Synthesis and Biological Evaluation of Novel Benzoxazinyl-Oxazolidinones as Potential Antibacterial Agents, Bioorganic & Medicinal Chemistry Letters, 2013, 3697-3699, 23.
Hickey et al., Experimental model of reversible myelosuppression caused by short-term, high-dose oxazolidinone administration, Therapy, 2006, 521-526, 3(4).
Lee, Myungsun, Linezolid for Treatment of Chronic Extensively Drug-Resistant Tuberculosis, The New England Journal of Medicine, 2012, p. 1508-1518, vol. 367, No. 16.
Shaw et al., The oxazolidinones: past, present, and future, Ann. N.Y. Acad. Sci., 2011, 48-70, 1241.
Suzuki, Hideyuki, et al., Potent Oxazolidinone Antibacterials with Heteroaromatic C-Ring Substructure, ACS Medicinal Chemistry Letters, 2013, p. 1074-1078, vol. 4.
Yang et al., Discovery of a Teraryl Oxazolidinone Compound (S)-N-((3-(3-Fluoro-4-(4-(pyridin-2-yl)-1H-pyrazol-1-yl) phenyl)-2-oxooxazolidin-5-yl)methyl)acetamide Phosphate as a Novel Antimicrobial Agent with Enhanced Safety Profile and Efficacies, Journal of Medicinal Chemistry, 2015, 6389-6409, 58.

\* cited by examiner

*Primary Examiner* — Rebecca L Anderson
(74) *Attorney, Agent, or Firm* — Janet E. Fair; Catherine D. Fitch

(57) ABSTRACT

The present invention relates to oxazolidinone Compounds of Formula (I): (I) and pharmaceutically acceptable salts thereof, wherein A, E, and R1 are as defined herein. The present invention also relates to compositions which comprise at least one oxazolidinone compound of the invention. The invention also provides methods for inhibiting growth of mycobacterial cells as well as a method of treating mycobacterial infections by Mycobacterium tuberculosis comprising administering a therapeutically effective amount of an oxazolidinone of the invention and/or a pharmaceutically acceptable salt thereof, or a composition comprising such compound and/or salt.

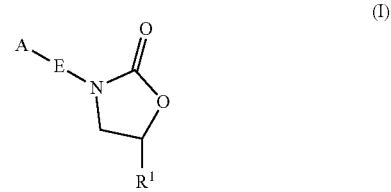

(I)

16 Claims, No Drawings

OXAZOLIDINONE COMPOUNDS AND METHODS OF USE THEREOF AS ANTIBACTERIAL AGENTS

CROSS-REFERENCE TO RELATED APPLICATIONS

This application is a U.S. National Phase application under 35 U.S.C. § 371 of PCT Application No. PCT/US2018/022531, filed Mar. 15, 2018, which published as WO2018/175185 A1 on Sep. 27, 2018, and claims priority under 35 U.S.C. § 365(b) from PCT Application No. PCT/CN2017/077256, filed Mar. 20, 2017.

FIELD OF THE INVENTION

The present invention relates to novel oxazolidinone compounds useful for the treatment of bacterial infections, particularly mycobacterial infections. The invention also relates to methods of use of oxazolidinone compounds for the treatment of mycobacterial infections such as those caused by Mycobacteria *tuberculosis*.

BACKGROUND OF THE INVENTION

*Mycobacterium* is a genus of bacterium, neither truly gram-positive nor truly gram-negative, including pathogens responsible for tuberculosis (*M. tuberculosis*) and leprosy (*M. leprae*). *Tuberculosis* (TB), in particular, despite the availability of anti-TB drugs such as isoniazide and rifampin, is considered to be one of the world's deadliest diseases. According to World Health Organization, in 2012, there were 8.6 million new TB cases and 1.3 million TB deaths. See, Global tuberculosis report 2013 published by the World Health Organization. Complicating the TB epidemic is the rising tide of multi-drug-resistant strains, and the deadly association with HIV. People who are HIV-positive and infected with TB are 30 times more likely to develop active TB than people who are HIV-negative and TB is responsible for the death of one out of every three people with HIV/AIDS worldwide. See, e.g., Kaufmann et al., *Trends Microbiol.* 1: 2-5 (1993) and Bloom et al., *N. Engl. J. Med.* 338: 677-678 (1998).

Mycobacteria other than *M. tuberculosis* are increasingly found in opportunistic infections that plague the AIDS patient. Organisms from the *M. avium*-intracellulare complex (MAC), especially serotypes four and eight, account for 68% of the mycobacterial isolates from AIDS patients. Enormous numbers of MAC are found (up to 1010 acid-fast bacilli per gram of tissue), and consequently, the prognosis for the infected AIDS patient is poor.

Oxazolidinones are a class of compounds containing 2-oxazolidone, a 5-membered ring containing nitrogen and oxygen, which are used as antimicrobials. See, e.g. WO 2009157423. In general, oxazolidinones are known to be monoamine oxidase inhibitors and to have activity against gram-positive microorganisms. WO 2006022794, Suzuki et al., *Med. Chem. Lett.* 4:1074-1078 (2013), Yang et al., *J. Med. Chem.* 58:6389-6409 (2015), Shaw et al., Ann. N.Y. Acad. Sci. 1241:48-70 (2011), Several oxazolidinone antibiotics have been approved or are in clinical trials for the treatment of gram-positive bacterial infections such as methicillin resistant *Staphylococcus aureus*. Examples of oxazolidinone antibiotics include linezolid (Zyvox™, Pfizer Inc., New York, N.Y.) and tedizolid (Sivextro™, Merck Sharp & Dohme Corp., Kenilworth, N.J.). Tedizolid is used to treat acute bacterial skin and skin structure infections caused by specific susceptible gram-positive bacteria. Linezolid is indicated for the treatment of several infections caused by susceptible strains of gram-positive microorganisms including nosocomial pneumonia, complicated skin and skin structure infections, and community-acquired pneumonia. In addition, it is currently being tested for the treatment of multi-drug resistant (MDR) and extensively drug-resistant (XDR) *Mycobacterium tuberculosis* (Mtb) in clinical trials. Lee et al., *N. Engl. J. Med* 367: 1508-18 (2012). Despite clinical efficacy in treating these diseases, long-term use of linezolid has been associated with adverse events including myelosuppression (including anemia and leukopenia) (Hickey et al., Therapy 3(4):521-526 (2006), neuropathy, and serotonin syndrome. These adverse events are hypothesized to be associated with the inhibition of mitochondrial protein synthesis. Flanagan et al., *Antimicrobial Agents and Chemotherapy* 59(1):178-185 (2015).

Development of oxazolidinone antibiotics that are safer than approved oxazolidinones yet at least as effective would greatly benefit Mtb patients.

SUMMARY OF THE INVENTION

The present invention is directed to certain novel oxazolidinone compounds which have antibacterial activity. The compounds, and their pharmaceutically acceptable salts, can be useful, for example, for the treatment of bacterial infections, for example, mycobacterial infections. More particularly, the present invention includes compounds of Formula I, or a pharmaceutically acceptable salt thereof:

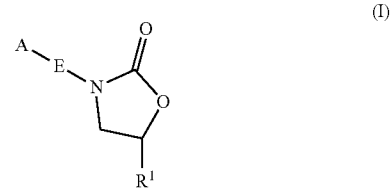

wherein:
$R^1$ is —$CH_2NHC(R^2)NR^3$;
$R^2$ is H, $C_1$-$C_6$ alkyl, or $NR^4R^5$;
$R^3$ is H, $C_1$-$C_6$ alkyl, or CN;
$R^4$ is H or $C_1$-$C_6$ alkyl;
$R^5$ is H or $C_1$-$C_6$ alkyl;
E is a 6-membered aryl or a 5- or 6-membered heteroaryl containing from one to three heteroatoms independently selected from S, O, and N, wherein said aryl and said heteroaryl are unsubstituted or substituted with up to four substituents, which are independently selected from halogen, $C_1$-$C_6$ alkyl, —CN, $C_1$-$C_6$ haloalkyl, —$CH_2NR^4R^5$, —$CH_2NHCOCH_3$, $C_1$-$C_6$ alkoxy, $C_1$-$C_6$ haloalkoxy, —OH, and $C_3$-$C_6$ cycloalkyl;
A is a 6-membered aryl or a 5- or 6-membered heteroaryl or heterocycle containing from one to three heteroatoms independently selected from S, O, and N, wherein the aryl, the heteroaryl and the heterocycle are unsubstituted or substituted with up to four substituents, which are independently selected from halogen, $C_1$-$C_6$ alkyl, —CN, $C_1$-$C_6$ haloalkyl, —$SO^2C_1$-$C_6$ alkyl, —$SO^2NR^4R^5$, $C_1$-$C_6$ alkoxy, $C_1$-$C_6$ haloalkoxy, —OH, oxo, tetrazole, triazole, and $C_3$-$C_6$ cycloalkyl, and wherein the tetrazole, triazole, and $C_3$-$C_6$ cycloalkyl are unsubstituted or substituted with up to three substituents selected from $C_1$-$C_6$ alkyl.

The present invention also relates to a pharmaceutical composition for treating a bacterial infection in a subject, particularly an *M. tuberculosis* infection, comprising an oxazolidinone compound of the invention and a pharmaceutically acceptable carrier, diluent or excipient.

The Compounds of Formula (I) (also referred to herein as the "Oxazolidinone Compounds") and pharmaceutically acceptable salts thereof can be useful, for example, for inhibiting the growth of *Mycobacterium tuberculosis*, and/or for treating or preventing tuberculosis in a patient. Without being bound by any specific theory, it is believed that uses of certain oxazolidinone compounds, including those described herein, for the treatment of tuberculosis are likely to cause less myelosuppression than known oxazolidinone compounds such as linezolid because they are not associated with a high degree of inhibition of mitochondrial protein synthesis, see PCT/US16/057257, hereby incorporated by reference. Additionally, oxazolidinone compounds, including those described herein, can be more selective than known oxazolidinone compounds, with weaker Gram-positive antibacterial activity and high potency against *M. tuberculosis*, see PCT/US16/057257, hereby incorporated by reference.

The present invention is also directed to 1) methods of treating tuberculosis in a subject in need of treatment thereof, comprising administering to the subject an effective amount of an oxazolidinone compound; and 2) uses of an oxazolidinone compound for the treatment of tuberculosis.

Embodiments are either described in or will be apparent from the ensuing description, examples and appended claims.

DETAILED DESCRIPTION OF THE INVENTION

In vitro testing of oxazolidinone compounds revealed such compounds have excellent potency in inhibiting the growth of *Mycobacteria tuberculosis*, but do not have strong Gram positive antibacterial activity; see PCT/US16/057257, hereby incorporated by reference. Compounds of Formula I and their pharmaceutically acceptable salts are expected to be useful for the treatment of *mycobacterial tuberculosis* (Mtb), yet not lead to the side effects such as myelosuppression that are associated with the oxazolidinone linezolid, which is approved for treatment of Gram-positive infections. Therefore, such compounds would have significant advantages over linezolid and analogs as Mtb therapeutic agents. The Compounds of Formula (I)

In one aspect, the present invention includes compounds of Formula I:

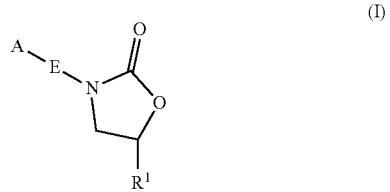

(I)

and pharmaceutically acceptable salts thereof, wherein A, E, and $R^1$ are defined above for the Compounds of Formula (I); wherein the compounds may be suitable for use for the treatment of bacterial infections, particularly mycobacterial infections.

In certain embodiments of the Compounds of Formula (I), described herein, $R^1$ is —$CH_2NHC(R^2)NR^3$ which can also be represented as —$CH_2NH$—$C(R^2)$=$NR^3$.

The compounds of the invention also include Compounds of Formula (II):

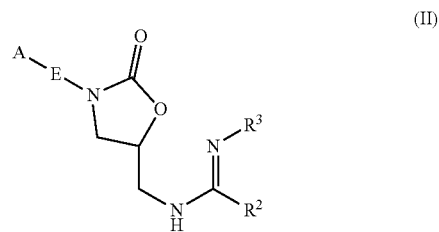

(II)

wherein, $R^2$ and $R^3$ and E and A are described below and contain the same meaning as when used with regard to the Compounds of Formula (I).

With regard to the Compounds of Formula (I) and (II), described herein, $R^2$ is hydrogen, $C_1$-$C_6$ alkyl or $NR^4R^5$. In certain embodiments of the Compounds of Formula (I) and (II), described herein, $R^2$ is hydrogen. In another embodiment, $R^2$ is $C_1$-$C_6$ alkyl. Suitable alkyls include, but are not limited to, methyl, ethyl, propyl, isopropyl, butyl, sec- and tert-butyl, pentyl, hexyl. In certain embodiments of the Compounds of Formula (I) and (II), described herein, $R^2$ is methyl.

In yet another embodiment $R^2$ is $NR^4R^5$. In such embodiments of the Compounds of Formula (I) and (II), described herein, wherein $R^2$ is $NR^4R^5$, $R^4$ is H or $C_1$-$C_6$ alkyl. In certain embodiments of the Compounds of Formula (I) and (II), described herein, $R^4$ is hydrogen. In other embodiments of the Compounds of Formula (I) and (II), described herein, $R^4$ is $C_1$-$C_6$ alkyl. Suitable alkyls include, but are not limited to, methyl, ethyl, propyl, isopropyl, butyl, sec- and tert-butyl, pentyl, and hexyl. In such embodiments of the Compounds of Formula (I) and (II), described herein, wherein $R^2$ is $NR^4R^5$, $R^5$ is H or $C_1$-$C_6$ alkyl. In certain embodiments of the Compounds of Formula (I) and (II), described herein, $R^5$ is hydrogen. In other embodiments of the Compounds of Formula (I) and (II), described herein, $R^5$ is $C_1$-$C_6$ alkyl. Suitable alkyls include, but are not limited to, methyl, ethyl, propyl, isopropyl, butyl, sec- and tert-butyl, pentyl, and hexyl. In certain embodiments of the Compounds of Formula (I) and (II), described herein, $R^4$ and $R^5$ are both hydrogen. In certain embodiments of the Compounds of Formula (I) and (II), described herein, $R^4$ is hydrogen and $R^5$ is methyl.

With regard to the Compounds of Formula (I) and (II), described herein, $R^3$ is hydrogen, $C_1$-$C_6$ alkyl or —CN. In certain embodiments of the Compounds of Formula (I) and (II), described herein, $R^3$ is hydrogen. In another embodiment, $R^3$ is $C_1$-$C_6$ alkyl. Suitable alkyls include, but are not limited to, methyl, ethyl, propyl, isopropyl, butyl, sec- and tert-butyl, pentyl, and hexyl. In certain embodiments of the Compounds of Formula (I) and (II), described herein, $R^3$ is —CN.

With regards to the Compounds of Formula (I) and (II), described herein, E is a 6-membered aryl or a 5- or 6-membered heteroaryl containing from one to three heteroatoms independently selected from S, O, and N, wherein the aryl and the heteroaryl are unsubstituted or substituted with up to four substituents, which are independently selected from halogen, $C_1$-$C_6$ alkyl, —CN, $C_1$-$C_6$ haloalkyl, —CH$_2$NR$^4$R$^5$, —CH$_2$NHCOCH$_3$, C$_1$-C$_6$ alkoxy, C$_1$-C$_6$ haloalkoxy, —OH, and C$_3$-C$_6$ cycloalkyl.

In certain embodiments of the Compounds of Formula (I) and (II), described herein, E is a 6-membered aryl. Suitable aryls include, but are not limited to, phenyl. In certain embodiments of the compounds described herein, E is phenyl. In certain embodiments of the compounds described herein, E is an unsubstituted 6-membered aryl. In certain embodiments of the compounds described herein, E is a substituted 6-membered aryl. In certain embodiments of the compounds described herein, E is an unsubstituted phenyl. In certain embodiments of the compounds described herein, E is a substituted phenyl.

In certain embodiments of the Compounds of Formula (I) and (II), described herein, E is a 5- or 6-membered heteroaryl containing from one to three heteroatoms independently selected from S, O and N. Suitable 5- or 6-membered heteroaryl include, but are not limited to, pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridyl, imidazo[2,1-b]thiazolyl. In certain embodiments of the Compounds of Formula (I) and (II), described herein, E is pyridyl.

In certain embodiments of the compounds described herein, E is an unsubstituted 5- or 6-membered heteroaryl containing from one to three heteroatoms independently selected from S, O, and N. In certain embodiments of the compounds described herein, E is a substituted 5- or 6-membered heteroaryl containing from one to three heteroatoms independently selected from S, O, and N. In certain embodiments of the compounds described herein, E is an unsubstituted pyridyl In certain embodiments of the compounds described herein, E is a substituted pyridyl.

In certain embodiments of the Compounds of Formula (I) and (II), described herein, E is independently selected from:

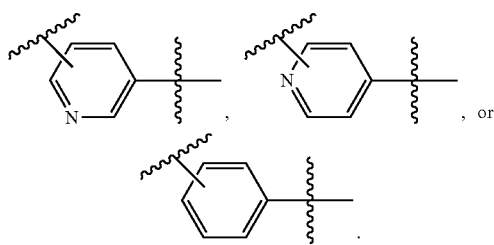

In such embodiments of the Compounds of Formula (I) and (II), described herein, E can be substituted with up to four substituents, which are independently selected from halogen, C$_1$-C$_6$ alkyl, —CN, C$_1$-C$_6$ haloalkyl, —CH$_2$NR$^4$R$^5$, —CH$_2$NHCOCH$_3$, C$_1$-C$_6$ alkoxy, C$_1$-C$_6$ haloalkoxy, —OH, and C$_3$-C$_6$ cycloalkyl. In certain embodiments of the Compounds of Formula (I) and (II), described herein, E can be substituted with one substituent independently selected from halogen, C$_1$-C$_6$ alkyl, —CN, C$_1$-C$_6$ haloalkyl, —CH$_2$NR$^4$R$^5$, —CH$_2$NHCOCH$_3$, C$_1$-C$_6$ alkoxy, C$_1$-C$_6$ haloalkoxy, —OH, and C$_3$-C$_6$ cycloalkyl. In certain embodiments of the Compounds of Formula (I) and (II), described herein, E can be substituted with two substituents independently selected from halogen, C$_1$-C$_6$ alkyl, —CN, C$_1$-C$_6$ haloalkyl, —CH$_2$NR$^4$R$^5$, —CH$_2$NHCOCH$_3$, C$_1$-C$_6$ alkoxy, C$_1$-C$_6$ haloalkoxy, —OH, and C$_3$-C$_6$ cycloalkyl. In certain embodiments of the Compounds of Formula (I) and (II), described herein, E can be substituted with three substituents independently selected from halogen, C$_1$-C$_6$ alkyl, —CN, C$_1$-C$_6$ haloalkyl, —CH$_2$NR$^4$R$^5$, —CH$_2$NHCOCH$_3$, C$_1$-C$_6$ alkoxy, C$_1$-C$_6$ haloalkoxy, —OH, and C$_3$-C$_6$ cycloalkyl. In certain embodiments of the Compounds of Formula (I) and (II), described herein, E can be substituted with four substituents independently selected from halogen, C$_1$-C$_6$ alkyl, —CN, C$_1$-C$_6$ haloalkyl, —CH$_2$NR$^4$R$^5$, —CH$_2$NHCOCH$_3$, C$_1$-C$_6$ alkoxy, C$_1$-C$_6$ haloalkoxy, —OH, and C$_3$-C$_6$ cycloalkyl.

In certain embodiments of the Compounds of Formula (I) and (II) described herein, E is substituted with halogen. Suitable halogens include, but are not limited to, fluorine, chlorine, iodine and bromine. In certain embodiments of the Compounds of Formula (I) and (II) described herein, E is substituted with C$_1$-C$_6$ alkyl. Suitable alkyls include, but are not limited to, methyl, ethyl, propyl, isopropyl, butyl, sec- and tert-butyl, pentyl, and hexyl. In certain embodiments of the Compounds of Formula (I) and (II) described herein, E is substituted with —CN. In certain embodiments of the Compounds of Formula (I) and (II) described herein, E is substituted with C$_1$-C$_6$ haloalkyl. Suitable haloalkyls include, but are not limited to, flouromethyl, difluoromethyl and trifluoromethyl. In certain embodiments of the Compounds of Formula (I) and (II) described herein, E is substituted with —CH$_2$NR$^4$R$^5$, wherein R$^4$ and R$^5$ are described above. In certain embodiments of the Compounds of Formula (I) and (II), described herein, E is substituted with —CH$_2$NHCOCH$_3$. In certain embodiments of the Compounds of Formula (I) and (II) described herein, E is substituted with C$_1$-C$_6$ alkoxy. Suitable alkoxys include, but are not limited to, methoxy, ethoxy and butoxy. In certain embodiments of the Compounds of Formula (I) and (II) described herein, E is substituted with C$_1$-C$_6$ haloalkoxy. Suitable haloalkoxys include, but are not limited to, mono-, di- or tri- fluoro methoxy. In certain embodiments of the Compounds of Formula (I) and (II) described herein, E is substituted with —OH. In certain embodiments of the Compounds of Formula (I) and (II) described herein, E is substituted with C$_3$-C$_6$ cycloalkyl. Suitable cycloalkyls include, but are not limited to, cyclopropyl, cyclobutyl, cyclopentyl, cyclohexyl.

In certain embodiments of the Compounds of Formula (I) and (II) described herein, E is unsubstituted phenyl or pyridyl. In certain embodiments of the Compounds of Formula (I) and (II) described herein, E is substituted phenyl or pyridyl substituted with one or two fluorines.

In certain embodiments of the Compounds of Formula (I) and (II), E is unsubstituted phenyl or unsubstituted pyridyl. In certain embodiments of the Compounds of Formula (I) and (II), E is phenyl substituted with one or two fluorines. In certain embodiments of the Compounds of Formula (I) and (II), E is pyridyl substituted with one or two fluorines.

With regard to the Compounds of Formula (I) and (II), A is a 6-membered aryl or a 5- or 6-membered heteroaryl or heterocycle containing from one to three heteroatoms independently selected from S, O, and N, wherein the aryl, the heteroaryl and the heterocycle are unsubstituted or substituted with up to four substituents, which are independently selected from halogen, C$_1$-C$_6$ alkyl, —CN, C$_1$-C$_6$ haloalkyl, —SO$^2$C$_1$-C$_6$ alkyl, —SO$^2$NR$^4$R$^5$, C$_1$-C$_6$ alkoxy, C$_1$-C$_6$ haloalkoxy, —OH, oxo, tetrazole, triazole, and C$_3$-C$_6$ cycloalkyl, and wherein the tetrazole, triazole, and C$_3$-C$_6$ cycloalkyl are unsubstituted or substituted with up to three substituents selected from C$_1$-C$_6$ alkyl.

In certain embodiments, A is a 6-membered aryl, wherein the aryl is unsubstituted or substituted with up to four substituents, which are independently selected from halogen, $C_1$-$C_6$ alkyl, —CN, $C_1$-$C_6$ haloalkyl, —$SO^2C_1$-$C_6$ alkyl, —$SO^2NR^4R^5$, $C_1$-$C_6$ alkoxy, $C_1$-$C_6$ haloalkoxy, —OH, oxo, tetrazole, triazole, and $C_3$-$C_6$ cycloalkyl, and wherein the tetrazole, triazole, and $C_3$-$C_6$ cycloalkyl are unsubstituted or substituted with up to three substituents selected from $C_1$-$C_6$ alkyl.

In certain embodiments of the Compounds of Formula (I) and (II), described herein, A is a 6-membered aryl. Suitable aryls include, but are not limited to, phenyl. In certain embodiments of the compounds described herein, A is phenyl. In certain embodiments of the compounds described herein, A is an unsubstituted 6-membered aryl. In certain embodiments of the compounds described herein, A is a substituted 6-membered aryl. In certain embodiments of the compounds described herein, A is an unsubstituted phenyl. In certain embodiments of the compounds described herein, A is a substituted phenyl.

In certain embodiments of the Compounds of Formula (I) and (II), described herein, A is a 5- or 6-membered heteroaryl containing from one to three heteratoms independently selected from S, O, and N. Suitable 5- or 6-membered heteroaryl include, but are not limited to, pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a] pyridyl, imidazo[2,1-b] thiazolyl. In certain embodiments of the Compounds of Formula (I) and (II), described herein, A is pyridyl, pyrazolyl or triazolyl or pyrazinyl.

In certain embodiments of the Compounds of Formula (I) and (II), described herein, A is a 5- or 6-membered heterocycle containing from one to three heteratoms independently selected from S, O, and N. Suitable 5- or 6-membered heterocycle include, but are not limited to, oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl. In certain embodiments of the Compounds of Formula (I) and (II), described herein, A is morpholinyl or thiomorpholinyl.

In certain embodiments of the Compounds of Formula (I) and (II), A is a 5-membered heteroaryl containing one heteroatom. In a further embodiment, A is a 5-membered heteroaryl containing two heteroatoms. In another embodiment A is a 5-membered heteroaryl containing three heteroatoms. In a still further embodiment A is a 5-membered heteroaryl containing four heteroatoms. In another embodiment, A is a 6-membered heteroaryl containing one heteroatom. In a further embodiment, A is a 6-membered heteroaryl containing two heteroatoms. In another embodiment A is a 6-membered heteroaryl containing three heteroatoms. In a still further sub-embodiment A is a 6-membered heteroaryl containing four heteroatoms.

In certain embodiments of the Compounds of Formula (I) and (II), A is a 5-membered heterocycle containing one heteroatom. In a further embodiment, A is a 5-membered heterocycle containing two heteroatoms. In another embodiment A is a 5-membered heterocycle containing three heteroatoms. In a still further embodiment A is a 5-membered heterocycle containing four heteroatoms. In another embodiment, A is a 6-membered heterocycle containing one heteroatom. In a further embodiment, A is a 6-membered heterocycle containing two heteroatoms. In another embodiment A is a 6-membered heterocycle containing three heteroatoms. In a still further sub-embodiment A is a 6-membered heterocycle containing four heteroatoms.

In certain embodiments of the Compounds of Formula (I) and (II), A is a monocyclic saturated or partially unsaturated ring optionally substituted with up to four substituents, which are independently selected from halogen, $C_1$-$C_6$ alkyl, —CN, $C_1$-$C_6$ haloalkyl, —$SO^2C_1$-$C_6$ alkyl, —$SO^2NR^4R^5$, $C_1$-$C_6$ alkoxy, $C_1$-$C_6$ haloalkoxy, —OH, oxo, tetrazole, triazole, and $C_3$-$C_6$ cycloalkyl, and wherein the tetrazole, triazole, and $C_3$-$C_6$ cycloalkyl are unsubstituted or substituted with up to three substituents selected from $C_1$-$C_6$ alkyl.

In certain embodiments of the Compounds of Formula (I) and (II), A is a 5-membered monocyclic saturated or partially unsaturated ring containing one heteroatom. In certain embodiments of the Compounds of Formula (I) and (II), A is a 5-membered monocyclic saturated or partially unsaturated ring containing two heteroatoms. In certain embodiments of the Compounds of Formula (I) and (II), A is a 5-membered monocyclic saturated or partially unsaturated ring containing three heteroatoms. In certain embodiments of the Compounds of Formula (I) and (II), A is a 5-membered monocyclic saturated or partially unsaturated ring containing four heteroatoms. In certain embodiments of the Compounds of Formula (I) and (II), A is a 6-membered monocyclic saturated or partially unsaturated ring containing one heteroatom. In certain embodiments of the Compounds of Formula (I) and (II), A is a 6-membered monocyclic saturated or partially unsaturated ring containing two heteroatoms. In certain embodiments of the Compounds of Formula (I) and (II), A is a 6-membered monocyclic saturated or partially unsaturated ring containing three heteroatoms. In certain embodiments of the Compounds of Formula (I) and (II), A is a 6-membered monocyclic saturated or partially unsaturated ring containing four heteroatoms.

In certain embodiments of the Compounds of Formula (I) and (II), A is unsubstituted. In certain embodiments of the Compounds of Formula (I) and (II), A is substituted with up to four substituents, which are independently selected from halogen, $C_1$-$C_6$ alkyl, —CN, $C_1$-$C_6$ haloalkyl, —$SO^2C_1$-$C_6$ alkyl, —$SO^2NR^4R^5$, $C_1$-$C_6$ alkoxy, $C_1$-$C_6$ haloalkoxy, —OH, oxo, tetrazole, triazole, and $C_3$-$C_6$ cycloalkyl, and wherein the tetrazole, triazole, and $C_3$-$C_6$ cycloalkyl are unsubstituted or substituted with up to three substituents selected from $C_1$-$C_6$ alkyl. In certain embodiments of the Compounds of Formula (I) and (II), A is substituted with four substituents, which are independently selected from halogen, $C_1$-$C_6$ alkyl, —CN, $C_1$-$C_6$ haloalkyl, —$SO^2C_1$-$C_6$ alkyl, —$SO^2NR^4R^5$, $C_1$-$C_6$ alkoxy, $C_1$-$C_6$ haloalkoxy, —OH, oxo, tetrazole, triazole, and $C_3$-$C_6$ cycloalkyl, and wherein the tetrazole, triazole, and $C_3$-$C_6$ cycloalkyl are unsubstituted or substituted with up to three substituents selected from $C_1$-$C_6$ alkyl. In other embodiments of the Compounds of Formula (I) and (II), A is substituted with three substituents, which are independently selected from halogen, $C_1$-$C_6$ alkyl, —CN, $C_1$-$C_6$ haloalkyl, —$SO^2C_1$-$C_6$ alkyl, —$SO^2NR^4R^5$, $C_1$-$C_6$ alkoxy, $C_1$-$C_6$ haloalkoxy, —OH, oxo, tetrazole, triazole, and $C_3$-$C_6$ cycloalkyl, and wherein the tetrazole, triazole, and $C_3$-$C_6$ cycloalkyl are unsubstituted or substituted with up to three substituents selected from $C_1$-$C_6$ alkyl. In yet other embodiments of the Compounds of Formula (I) and (II), A is substituted with two substituents, which are independently selected from halogen, $C_1$-$C_6$ alkyl, —CN, $C_1$-$C_6$ haloalkyl, —$SO^2C_1$-$C_6$ alkyl, —$SO^2NR^4R^5$, $C_1$-$C_6$ alkoxy, $C_1$-$C_6$ haloalkoxy, —OH, oxo, tetrazole, triazole, and $C_3$-$C_6$ cycloalkyl, and wherein the tetrazole, triazole, and $C_3$-$C_6$ cycloalkyl are unsubstituted or substituted with up to three substituents selected from $C_1$-$C_6$ alkyl. In yet a further embodiment of the Compounds of Formula (I) and (II), A is substituted with a single substituent, which is independently selected from halogen, $C_1$-$C_6$ alkyl, —CN, $C_1$-$C_6$ haloalkyl, —$SO^2C_1$-$C_6$ alkyl, —$SO^2NR^4R^5$, $C_1$-$C_6$ alkoxy, $C_1$-$C_6$ haloalkoxy, —OH, oxo, tetrazole, triazole, and $C_3$-$C_6$ cycloalkyl, and wherein the tetrazole, triazole, and $C_3$-$C_6$ cycloalkyl are unsubstituted or substituted with up to three substituents selected from $C_1$-$C_6$ alkyl.

In certain embodiments of the Compounds of Formula (I) and (II), A is substituted with up to four substituents independently selected from halogen, $C_1$-$C_6$ alkyl, —CN, $C_1$-$C_6$ haloalkyl, —$SO^2C_1$-$C_6$ alkyl, —$SO^2NR^4R^5$, $C_1$-$C_6$ alkoxy, $C_1$-$C_6$ haloalkoxy, —OH, oxo, tetrazole, triazole, and $C_3$-$C_6$ cycloalkyl, and wherein the tetrazole, triazole, and $C_3$-$C_6$ cycloalkyl are unsubstituted or substituted with up to three substituents selected from $C_1$-$C_6$ alkyl.

In certain embodiments of the Compounds of Formula (I) and (II) described herein, A is substituted with halogen. Suitable halogens include, but are not limited to, fluorine, chlorine, iodine and bromine. In certain embodiments of the Compounds of Formula (I) and (II) described herein, A is substituted with $C_1$-$C_6$ alkyl. Suitable alkyls include, but are not limited to, methyl, ethyl, propyl, isopropyl, butyl, sec- and tert-butyl, pentyl, and hexyl. In certain embodiments of the Compounds of Formula (I) and (II) described herein, A is substituted with —CN. In certain embodiments of the Compounds of Formula (I) and (II) described herein, A is substituted with $C_1$-$C_6$ haloalkyl. Suitable haloalkyls include, but are not limited to, flouromethyl, difluoromethyl and trifluoromethyl. In certain embodiments of the Compounds of Formula (I) and (II) described herein, A is substituted with —$SO^2C_1$-$C_6$ alkyl. Suitable —$SO^2C_1$-$C_6$ alkyls include, but are not limited to, —$SO^2CH^3$. In certain embodiments of the Compounds of Formula (I) and (II) described herein, A is substituted with —$SO^2NR^4R^5$. Suitable —$SO^2NR^4R^5$s include, but are not limited to, —$SO^2NH^2$. In certain embodiments of the Compounds of Formula (I) and (II) described herein, A is substituted with $C_1$-$C_6$ alkoxy. Suitable alkoxys include, but are not limited to, methoxy, ethoxy and butoxy. In certain embodiments of the Compounds of Formula (I) and (II) described herein, A is substituted with $C_1$-$C_6$ haloalkoxy. Suitable haloalkoxys include, but are not limited to, mono, di or tri fluoro methoxy. In certain embodiments of the Compounds of Formula (I) and (II) described herein, A is substituted with —OH. In certain embodiments of the Compounds of Formula (I) and (II) described herein, A is substituted with oxo. In certain embodiments of the Compounds of Formula (I) and (II) described herein, A is substituted with tetrazole. In certain embodiments of the Compounds of Formula (I) and (II) described herein, A is substituted with triazole. In certain embodiments of the Compounds of Formula (I) and (II) described herein, A is substituted with $C_3$-$C_6$ cycloalkyl. Suitable cycloalkyls include, but are not limited to, cyclopropyl, cyclobutyl, cyclopentyl, cyclohexyl.

In certain embodiments of the Compounds of Formula (I) and (II) described herein, when A is tetrazole, triazole, and $C_3$-$C_6$ cycloalkyl, the tetrazole, triazole, and $C_3$-$C_6$ cycloalkyl are unsubstituted. In certain embodiments of the Compounds of Formula (I) and (II) described herein, when A is tetrazole, triazole, and $C_3$-$C_6$ cycloalkyl, the tetrazole, triazole, and $C_3$-$C_6$ cycloalkyl are substituted with up to three substituents selected from $C_1$-$C_6$ alkyl. In certain embodiments of the Compounds of Formula (I) and (II) described herein, when A is tetrazole, triazole, and $C_3$-$C_6$ cycloalkyl, the tetrazole, triazole, and $C_3$-$C_6$ cycloalkyl are substituted with three substituents selected from $C_1$-$C_6$ alkyl. In certain embodiments of the Compounds of Formula (I) and (II) described herein, when A is tetrazole, triazole, and $C_3$-$C_6$ cycloalkyl, the tetrazole, triazole, and $C_3$-$C_6$ cycloalkyl are substituted with two substituents selected from $C_1$-$C_6$ alkyl. In certain embodiments of the Compounds of Formula (I) and (II) described herein, when A is tetrazole, triazole, and $C_3$-$C_6$ cycloalkyl, the tetrazole, triazole, and $C_3$-$C_6$ cycloalkyl are substituted with one substituent selected from $C_1$-$C_6$ alkyl. In certain embodiments of the Compounds of Formula (I) and (II) described herein, when A is tetrazole or triazole, the tetrazole or triazole is substituted with methyl.

In certain embodiments of the Compounds of Formula (I) and (II), or a pharmaceutically acceptable salt thereof, A is selected from:

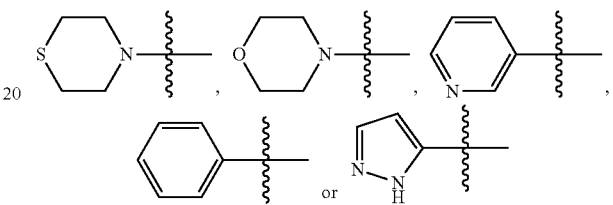

wherein A is unsubstituted or substituted with up to four substituents independently selected from halogen, $C_1$-$C_6$ alkyl, —CN, $C_1$-$C_6$ haloalkyl, —$SO^2C_1$-$C_6$ alkyl, —$SO^2NR^4R^5$, $C_1$-$C_6$ alkoxy, $C_1$-$C_6$ haloalkoxy, —OH, oxo, tetrazole, triazole, and $C_3$-$C_6$ cycloalkyl, and wherein the tetrazole, triazole, and $C_3$-$C_6$ cycloalkyl are unsubstituted or substituted with up to three substituents selected from $C_1$-$C_6$ alkyl.

In another embodiment of the Compounds of Formula (I) and (II), A is:

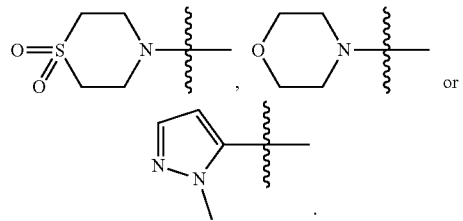

Another embodiment of the Compounds of Formula (I) or (II), or a pharmaceutically acceptable salt thereof, is wherein A is phenyl substituted with one substituent independently selected from —$SO^2C_1$-$C_6$ alkyl or —$SO^2NR^4R^5$.

Another embodiment of the Compounds of Formula (I) or (II), or a pharmaceutically acceptable salt thereof, is wherein A is phenyl substituted with one substituent independently selected from —$SO^2CH_3$ or —$SO^2NH^2$.

Another embodiment of the Compounds of Formula (I) or (II), or a pharmaceutically acceptable salt thereof, is wherein A is pyridyl substituted with one substituent independently selected from —$SO^2C_1$-$C_6$ alkyl, tetrazole or triazole, and wherein the tetrazole, or triazole are unsubstituted or substituted with up to three substituents selected from $C_1$-$C_6$ alkyl.

Another embodiment of the Compounds of Formula (I) or (II), or a pharmaceutically acceptable salt thereof, is wherein A is pyridyl substituted with one substituent independently selected from —$SO^2CH_3$, 1H-tetrazol-1-yl, 5-methyl-2H-tetrazol-2-yl, 2H-1,2,3-triazol-2-yl.

Other embodiments described herein include the following:

(a) A pharmaceutical composition comprising an effective amount of a compound of Formula (I) or (II), as defined herein, or a pharmaceutically acceptable salt thereof, and a pharmaceutically acceptable carrier.

(b) The pharmaceutical composition of (a), further comprising a second compound, wherein the second compound is an antibiotic.

(c) The pharmaceutical composition of (b), wherein the second compound is selected from the group consisting of: ethambutol, pyrazinamide, isoniazid, levofloxacin, moxifloxacin, gatifloxacin, ofloxacin, kanamycin, amikacin, capreomycin, streptomycin, ethionamide, prothionamide, cycloserine, terid900ne, para-aminosalicylic acid, clofazimine, clarithromycin, amoxicillin-clavulanate, thiacetazone, meropenem-clavulanate, and thioridazine.

(d) A pharmaceutical composition comprising (i) a compound of Formula (I) or (II), or a pharmaceutically acceptable salt thereof, and (ii) a second compound, wherein the second compound is an antibiotic, wherein the compound of Formula (I) or (II), and the second compound are each employed in an amount that renders the combination effective for treating or preventing bacterial infection.

(e) The combination of (d), wherein the second compound is selected from the group consisting of: ethambutol, pyrazinamide, isoniazid, levofloxacin, moxifloxacin, gatifloxacin, ofloxacin, kanamycin, amikacin, capreomycin, streptomycin, ethionamide, prothionamide, cycloserine, teridione, para-aminosalicylic acid, clofazimine, clarithromycin, amoxicillin-clavulanate, thiacetazone, meropenem-clavulanate, and thioridazine.

(f) A method for treating a bacterial infection in a subject which comprises administering to a subject in need of such treatment an effective amount of a compound of Formula (I) or (II), or a pharmaceutically acceptable salt thereof (g) A method for preventing and/or treating a bacterial infection which comprises administering to a subject in need of such treatment an effective amount of a compound of Formula (I) or (II), or a pharmaceutically acceptable salt thereof (h) A method for treating a bacterial infection which comprises administering to a subject in need of such treatment a therapeutically effective amount of the composition of (a), (b), (c), (d), or (e).

(i) The method of treating a bacterial infection as set forth in (f), (g), or (h), wherein the bacterial infection is due to Mycobacterium tuberculosis.

(j) A method for preventing and/or treating a mycobacterial infection which comprises administering to a subject in need of such treatment an effective amount of a composition comprising an oxazolidinone compound of Formula (I) or (II), or a pharmaceutically acceptable salt thereof.

(k) The method of treating a mycobacterial infection as set forth in (j), wherein the mycobacterial infection is due to M tuberculosis.

(l) The method of treating a mycobacterial infection as set forth in (j), wherein the composition is a composition of (a), (b), (c), (d), or (e).

The present invention also includes a compound of Formula (I) or (II), or a pharmaceutically acceptable salt thereof, (i) for use in, (ii) for use as a medicament for, or (iii) for use in the preparation (or manufacture) of a medicament for, medicine or treating bacterial infection, particularly a mycobacterial infection. In these uses, the compounds of the present invention can optionally be employed in combination with one or more second therapeutic agents including ethambutol, pyrazinamide, isoniazid, levofloxacin, moxifloxacin, gatifloxacin, ofloxacin, kanamycin, amikacin, capreomycin, streptomycin, ethionamide, prothionamide, cycloserine, teridione, para-aminosalicylic acid, clofazimine, clarithromycin, amoxicillin-clavulanate, thiacetazone, meropenem-clavulanate, and thioridazine.

Additional embodiments of the invention include the pharmaceutical compositions, combinations and methods set forth in (a)-(l) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (l) above are understood to include all embodiments of the compounds and/or salts, including such embodiments as result from combinations of embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula (I) or (II) or its salt and a pharmaceutically acceptable carrier and optionally one or more excipients, it is understood that the term "substantially pure" is in reference to a compound of Formula (I) or (II) or its salt per se; i.e., the purity of the active ingredient in the composition.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "-O-alkyl," etc.

As used herein, and throughout this disclosure, the following terms, unless otherwise indicated, shall be understood to have the following meanings:

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, and the like.

"Antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent.

"About", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1, 0.2, 0.3, 0.4, 0.5, 1.0, 2.0, 3.0, 4.0, or 5.0 of the appropriate unit. In certain embodiments, "about" can mean a variation of ±1%, 2%, 3%, 4%, 5%, 10%, or 20%.

"Aromatic ring system" means monocyclic, bicyclic or tricyclic aromatic ring or ring system containing 5-14 ring atoms, wherein at least one of the rings is aromatic. Aromatic ring systems, as used herein, encompass aryls and heteroaryls. The term may be used to describe a carbocyclic ring fused to an aryl group. For example, a 5-7-membered cycloalkyl can be fused through two adjacent ring atoms to a 5-6-membered heteroaryl containing 1, 2, or 3 heteroatom ring atoms selected from N, O, and S. In another example, a heteromonocyclic ring is fused through two ring atoms to a phenyl or 5-6-membered heteroaryl containing 1, 2, or 3 heteroatoms selected from N, O, and S.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl.

As used herein, e.g. in the definition of $R^1$, "—$CH_2NHC(R^2)NR^3$" means "—$CH_2NH$—$C(R^2)$=$NR^3$".

"Drug resistant" means, in connection with a Mycobacterium, a Mycobacterium which is no longer susceptible to at least one previously effective drug; which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs.

"Halogen" includes fluorine, chlorine, bromine and iodine.

"Heteroaryl", as used herein, refers to an monocyclic or multicyclic ring system comprising about 5 to about 14 ring atoms, wherein from 1 to 4 of the ring atoms is independently O, N, or S and the remaining ring atoms are carbon atoms, wherein at least one of the heteroatom containing rings is aromatic. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof In another embodiment of the present invention, heteroaryl is pyridine. Examples of bicyclic rings include:

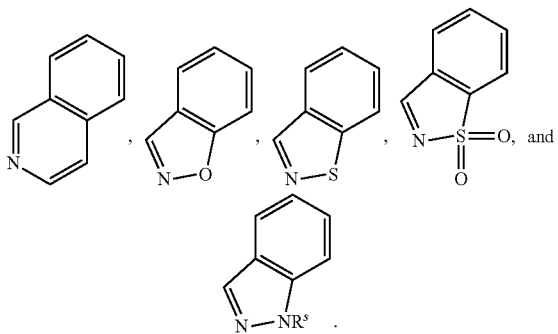

"Heterocycle " means a monocyclic or bicyclic saturated, partially unsaturated, or unsaturated ring system containing 5-10 atoms and containing at least one ring heteroatom selected from N, S and O. In select embodiments, the ring system contains 1-4 heteroatoms selected from N, S and O. When a heterocycle contains two rings, the rings may be fused, bridged or spirocyclic. Examples of monocyclic heterocycle rings include piperazine, piperidine, and morpholine. Examples of bicyclic heterocycle rings include 1,4-diazabicyclo[2,2,2]octane and 2,6-diazaspiroheptane.

"Oxo" means an oxygen atom connected to another atom by a double bond and is can be represented "=O".

"Tuberculosis" comprises disease states usually associated with infections caused by mycobacteria species comprising M. tuberculosis complex. The term "tuberculosis" is also associated with mycobacterial infections caused by mycobacteria other than M. tuberculosis (MOTT). Other mycobacterial species include M. avium-intracellulare, M. kansarii, M. fortuitum, M. chelonae, M. leprae, M. africanum, and M. microti, M. avium paratuberculosis, M. intracellulare, M. scrofulaceum, M. xenopi, M. marinum, and M. ulcerans.

Another embodiment of the present invention is a compound of Formula (I) or (II), or a pharmaceutically acceptable salt thereof, as originally defined or as defined in any of the foregoing embodiments, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula (I) or (II) or a salt of Formula (I) or (II) (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

The present invention encompasses all stereoisomeric forms of the compounds of Formula (I) and Formula (II). Unless a specific stereochemistry is indicated, the present invention is meant to comprehend all such isomeric forms of these compounds. Centers of asymmetry that are present in the compounds of Formula (I) and Formula (II) can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, Formula IA, or Formula IB or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. Unless a particular isomer, salt, solvate (including hydrates) or solvated salt of such racemate, enantiomer, diastereomer or tautomer is indicated, the present invention includes all such isomers, as well as salts, solvates (including hydrates) and solvated salts of such racemates, enantiomers, diastereomers and tautomers and mixtures thereof.

When any variable (e.g., $R^4$, $R^5$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described last, preceded by the adjacent functionality toward the point of attachment.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" means that one or more hydrogens on the designated atom is replaced with a selection from the indicated group, provided that the designated atom's normal valency under the existing circumstances is not exceeded, and that the substitution results in a stable compound. The term substituted shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

By "stable compound" or "stable structure" is meant a compound that is sufficiently robust to survive isolation to a useful degree of purity from a reaction mixture, and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I.

When a group, e.g., $C_1$-$C_8$ alkyl, is indicated as being substituted, such substitutions can also occur where such group is part of a larger substituent, e.g., —$C_1$-$C_6$alkyl-$C_3$-$C_7$cycloalkyl and —$C_1$-$C_8$alkyl-aryl.

In the Compounds of Formula (I) and Formula (II), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula (I) and Formula (II). For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula (I) and Formula (II) can be prepared without undue experimentation by conventional techniques well known to those skilled in the art or by processes analogous to those described in the EXAMPLES herein using appropriate isotopically-enriched reagents and/or intermediates.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaryl described as containing from "one to three heteroatoms" means the ring can contain 1, 2 or 3 heteroatoms. It is also to be understood that any range cited herein includes within its scope all of the sub-ranges within that range. Thus, for example, a heteroaryl described as containing from "one to three heteroatoms" is intended to include as aspects thereof, heterocyclic rings containing 1 or 2 heteroatoms, 2 or 3 heteroatoms, 1 to 3 heteroatoms, 1 heteroatom, 2 heteroatoms, and 3 heteroatoms. Similarly, $C_1$-$C_6$ when used with a chain, for example an alkyl chain, means that the chain can contain 1, 2, 3, 4, 5 or 6 carbon atoms. It also includes all ranges contained therein including $C_1$-$C_5$, $C_1$-$C_4$, $C_1$-$C_3$, $C_1$-$C_2$, $C_2$-$C_6$, $C_3$-$C_6$, $C_4$-$C_6$, $C_5$-$C_6$, and all other possible combinations.

It should also be noted that any carbon as well as heteroatom with unsatisfied valences in the text, schemes, examples and tables herein is assumed to have the sufficient number of hydrogen atom(s) to satisfy the valences.

When any substituent or variable occurs more than one time in any constituent or in Formula (I), its definition on each occurrence is independent of its definition at every other occurrence, unless otherwise indicated.

The term "compound" refers to the free compound and, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. It will be understood that, as used herein, the compounds of the instant invention can also include the pharmaceutically acceptable salts, and also salts that are not pharmaceutically acceptable when they are used as precursors to the free compounds or their pharmaceutically acceptable salts or in other synthetic manipulations.

The term "pharmaceutically acceptable salt" refers to a salt which possesses the effectiveness of the parent compound and which is not biologically or otherwise undesirable (e.g., is neither toxic nor otherwise deleterious to the recipient thereof). The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The compounds of the invention can also be employed in the form of a prodrug. For example, the hydrogen in —COOH be replaced with any the following groups: $C_{1-6}$ alkyl, $C_{3-6}$ cycloalkyl, —$C_{1-6}$alkyl-$C_{3-6}$cycloalkyl, $C_{3-7}$ cycloheteroalkyl, —$C_{1-6}$alkyl-$C_{3-7}$cycloheteroalkyl, aryl, —$C_{1-10}$alkyl-aryl, heteroaryl, and —$C_{1-10}$ alkyl-heteroaryl. Any $C_{1-6}$ alkyl, $C_{3-6}$ cycloalkyl, or $C_{3-7}$ cycloheteroalkyl can also be substituted. Any aryl or heteroaryl can also be substituted as indicated.

As set forth above, the present invention includes pharmaceutical compositions comprising a compound of Formula (I) or (II) of the present invention, optionally one or more other active components, and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof Thus, compositions according to the invention may, in addition to the inhibitor, contain diluents, fillers, salts, buffers, stabilizers, solubilizers, and other materials well known in the art.

Also as set forth above, the present invention includes a method for treating a bacterial infection which comprises administering to a subject in need of such treatment a therapeutically effective amount of a compound of Formula (I) or (II) or a pharmaceutically acceptable salt thereof. The term "subject" (or, alternatively, "patient") as used herein refers to an animal, preferably a mammal, most preferably a human, who has been the object of treatment, observation or experiment. The term "administration" and variants thereof (e.g., "administering" a compound) in reference to a compound of Formula (I) or (II) mean providing the compound, or a pharmaceutically acceptable salt thereof, to the individual in need of treatment. When a compound or a salt thereof is provided in combination with one or more other active agents, "administration" and its variants are each understood to include provision of the compound or its salt and the other agents at the same time or at different times. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" as used herein with respect to an oxazolidinone compound means the amount of active compound sufficient to cause a bacteriocidal or bacteriostatic effect. In one embodiment, the effective amount is a "therapeutically effective amount" meaning the amount of active compound that can overcome bacterial drug resistance and which is sufficient to inhibit bacterial replication and/or result in bacterial killing. When the active compound (i.e., active ingredient) is administered as the salt, references to the amount of active ingredient are to the free acid or free base form of the compound.

The administration of a composition of the present invention is suitably parenteral, oral, sublingual, transdermal, topical, intranasal, intratracheal, intraocular, or intrarectal, wherein the composition is suitably formulated for administration by the selected route using formulation methods well known in the art, including, for example, the methods for preparing and administering formulations described in chapters 39, 41, 42, 44 and 45 in Remington—The Science and Practice of Pharmacy, 21$^{st}$ edition, 2006. In one embodiment, compounds of the invention are administered intravenously in a hospital setting. In another embodiment, administration is oral in the form of a tablet or capsule or the like. The dosage of the compounds of the invention and of their pharmaceutically acceptable salts may vary within wide limits and should naturally be adjusted, in each particular case, to the individual conditions and to the pathogenic agent to be controlled. In general, for a use in the treatment of bacterial infections, the daily dose may be between 0.005 mg/kg to 100 mg/kg, 0.01 mg/kg to 10 mg/kg, 0.05 mg/kg to 5 mg/kg, 0.05 mg/kg to 1 mg/kg.

In some embodiments, the compound of the invention is provided in a pharmaceutical formulation for oral, intravenous, intramuscular, nasal, or topical administration. Thus, in some embodiments, the formulation can be prepared in a dosage form, such as but not limited to, a tablet, capsule, liquid (solution or suspension), suppository, ointment, cream, or aerosol. In some embodiments, the presently disclosed subject matter provides such compounds and/or formulations that have been lyophilized and that can be reconstituted to form pharmaceutically acceptable formulations for administration, for example, as by intravenous or intramuscular injection.

Intravenous administration of a compound of the invention can be conducted by reconstituting a powdered form of the compound with an acceptable solvent. Suitable solvents include, for example, saline solutions (e.g., 0.9% Sodium Chloride Injection) and sterile water (e.g., Sterile Water for Injection, Bacteriostatic Water for Injection with methylparaben and propylparaben, or Bacteriostatic Water for Injection with 0.9% benzyl alcohol). The powdered form of the compound can be obtained by gamma-irradiation of the compound or by lyophilization of a solution of the compound, after which the powder can be stored (e.g., in a sealed vial) at or below room temperature until it is reconstituted. The concentration of the compound in the reconstituted IV solution can be, for example, in a range of from about 0.1 mg/mL to about 20 mg/mL.

The methods of the presently disclosed subject matter are useful for treating these conditions in that they inhibit the onset, growth, or spread of the condition, cause regression of the condition, cure the condition, or otherwise improve the general well-being of a subject afflicted with, or at risk of, contracting the condition. Thus, in accordance with the presently disclosed subject matter, the terms "treat", "treating", and grammatical variations thereof, as well as the phrase "method of treating", are meant to encompass any desired therapeutic intervention, including but not limited to a method for treating an existing infection in a subject, and a method for the prophylaxis (i.e., preventing) of infection, such as in a subject that has been exposed to a microbe as disclosed herein or that has an expectation of being exposed to a microbe as disclosed herein.

Infections that may be treatable by the compounds of the invention can be caused by a variety of microbes, including fungi, algae, protozoa, bacteria, and viruses. In some embodiments, the infection is a bacterial infection. Exemplary microbial infections that may be treated by the methods of the invention include, but are not limited to, infections caused by one or more of *Staphylococcus aureaus, Enterococcus faecalis, Bacillus anthracis*, a *Streptococcus* species (e.g., *Streptococcus pyogenes* and *Streptococcus pneumoniae*), *Escherichia coli, Pseudomonas aeruginosa, Burkholderia cepacia*, a *Proteus* species (e.g., *Proteus mirabilis* and *Proteus vulgaris*), *Klebsiella pneumoniae, Acinetobacter baumannii, Strenotrophomonas maltophillia, Mycobacterium tuberculosis, Mycobacterium bovis, Nontuberculous mycobacteria* (NTM), other mycobacteria of the tuberculosis complex, and non-tuberculous mycobacteria, including *Mycobacterium ulcerans*.

In certain embodiments, the infection is an infection of a gram-positive bacterium. In some embodiments, the infection is selected from a mycobacterial infection, a *Bacillus anthracis* infection, an *Enterococcus faecalis* infection, and a *Streptococcus pneumoniae* infection.

In some embodiments, the compound of Formula (I) or (II) is administered prophylactically to prevent or reduce the incidence of one of: (a) a *Mycobacterium tuberculosis* infection in a subject at risk of infection; (b) a recurrence of a *Mycobacterium tuberculosis* infection; and (c) combinations thereof. In some embodiments, the compound of Formula (I) or (II) is administered to treat an existing *Mycobacterium tuberculosis* infection. In some embodiments, the compound of Formula (I) or (II) is administered to treat an infection of a multi-drug resistant strain of

*Mycobacterium tuberculosis* (i.e., a strain that is resistant to two or more previously known anti-tuberculosis drugs, such as isoniazid, ethambutol, rifampicin, kanamycin, capreomycin, linezolid, and streptomycin). In some embodiments, the compound of Formula (I) has a minimum inhibitory concentration (MIC) against *Mycobacterium tuberculosis* of 25 µg/mL or less. In some embodiments, the compound of Formula (I) or (II) is administered to treat an infection of a multi-drug resistant strain of *Mycobacterium tuberculosis*.

Thus, the methods of the presently disclosed subject matter can be useful for treating tuberculosis in that they inhibit the onset, growth, or spread of a TB infection, cause regression of the TB infection, cure the TB infection, or otherwise improve the general well-being of a subject afflicted with, or at risk of, contracting tuberculosis.

Subjects suffering from an *M. tuberculosis* or other tuberculosis-related infection can be determined via a number of techniques, e.g., sputum smear, chest X-ray, tuberculin skin test (i.e., Mantoux test or PPD test) and/or the presence of other clinical symptoms (e.g., chest pain, coughing blood, fever, night sweats, appetite loss, fatigue, etc.). If desired, bacterial RNA, DNA or proteins can be isolated from a subject believed to be suffering from TB and analyzed via methods known in the art and compared to known nucleic or amino acid sequences of bacterial RNA, DNA or protein.

In some embodiments, the compound of Formula (I) or (II) has a minimum inhibitory concentration (MIC) against *Mycobacterium tuberculosis* of 25 µg/mL or less. MICs can be determined via methods known in the art, for example, as described in Hurdle et al., 2008, *J. Antimicrob. Chemother.* 62:1037-1045.

In certain embodiments, microbial infections that may be treated by the methods of the invention include, but are not limited to, bacterial infection due to *Nontuberculous mycobacteria* (NTM). NTM species include, but are not limted to, *M. avium complex, M. abcessus, M. bolletii, M. kansasii, M. simiae* and *M. marinum*.

In some embodiments, the compound of Formula (I) or (II) is administered prophylactically to prevent or reduce the incidence of Hansen's disease or leprosy, such as *M. leprae* and *M. lepromatosis*.

In some embodiments, the methods of the invention further comprise administering to the subject an additional therapeutic compound. In some embodiments, the compound of the invention is administered to the subject before, after, or at the same time as one or more additional therapeutic compounds. In some embodiments, the additional therapeutic compound is an antibiotic. In some embodiments, the additional therapeutic compound is an anti-tuberculosis therapeutic. In some embodiments, the additional therapeutic compound is selected from the group comprising isoniazid, ethambutol, rifampicin, kanamycin, capreomycin, linezolid, and streptomycin. In some embodiments, the additional therapeutic compound is selected from the group comprising bedaquiline, ciprofloxacin, enviomycin, meropenem-clavulanate, ofloxacin, para-aminosalicylic acid, rifabutin, streptomycin and viomycin.

The invention thus provides in a further aspect, a combination comprising a compound of Formula (I) or (II) or a pharmaceutically acceptable salt thereof, together with one or more additional therapeutic agents. Examples of such one or more additional therapeutic agents are anti-tuberculosis agents including, but not limited to, amikacin, aminosalicylic acid, capreomycin, cycloserine, ethambutol, ethionamide, isoniazid, kanamycin, pyrazinamide, rifamycins (such as rifampin, rifapentine and rifabutin), streptomycin, clarithromycin, azithromycin, oxazolidinones and fluoroquinolones (such as ofloxacin, ciprofloxacin, moxifloxacin and gatifloxacin). Such chemotherapy is determined by the judgment of the treating physician using preferred drug combinations. "First-line" chemotherapeutic agents used to treat a *Mycobacterium tuberculosis* infection that is not drug resistant include isoniazid, rifampin, ethambutol, streptomycin and pyrazinamide. "Second-line" chemotherapeutic agents used to treat a *Mycobacterium tuberculosis* infection that has demonstrated drug resistance to one or more "first-line" drugs include ofloxacin, ciprofloxacin, ethionamide, aminosalicylic acid, cycloserine, amikacin, kanamycin and capreomycin. In addition to the aforementioned, there are a number of new anti-tuberculosis therapeutic agents emerging from clinical studies that may also be employed as the one or more additional therapeutic agents in a combination with a compound of Formula (I) or (II) including, but not limited to, TMC-207, OPC-67683, PA-824, LL-3858 and SQ-109.

Thus, the other antibiotic which may be combined with the compounds of Formula (I) or (II), are for example rifampicin (=rifampin); isoniazid; pyrazinamide; amikacin; ethionamide; moxifloxacin; ethambutol; streptomycin; para-aminosalicylic acid; cycloserine; capreomycin; kanamycin; thioacetazone; quinolones/fluoroquinolones such as for example ofloxacin, ciprofloxacin, sparfloxacin; macrolides such as for example clarithromycin, clofazimine, amoxicillin with clavulanic acid; rifamycins; rifabutin; rifapentine.

In a further aspect, the one or more additional therapeutic agent is, for example, an agent useful for the treatment of tuberculosis in a mammal, therapeutic vaccines, anti-bacterial agents, anti-viral agents; antibiotics and/or agents for the treatment of HIV/AIDS. Examples of such therapeutic agents include isoniazid (INH), ethambutol, rifampin, pirazinamide, streptomycin, capreomycin, ciprofloxacin and clofazimine.

In one aspect, the one or more additional therapeutic agent is a therapeutic vaccine. A compound of Formula (I) or (II) or a pharmaceutically acceptable salt thereof, may thus be administered in conjunction with vaccination against mycobacterial infection, in particular vaccination against *Mycobacterium tuberculosis* infection. Existing vaccines against mycobacterial infection include *Bacillus* Calmette Guerin (BCG). Vaccines currently under development for the treatment, prophylaxis or amelioration of mycobacterial infection include: modified BCG strains which recombinantly express additional antigens, cytokines and other agents intended to improve efficacy or safety; attenuated mycobacteria which express a portfolio of antigens more similar to *Mycobacterium tuberculosis* than BCG; and subunit vaccines. Subunit vaccines may be administered in the form of one or more individual protein antigens, or a fusion or fusions of multiple protein antigens, either of which may optionally be adjuvanted, or in the form of a polynucleotide encoding one or more individual protein antigens, or encoding a fusion or fusions of multiple protein antigens, such as where the polynucleotide is administered in an expression vector. Examples of subunit vaccines include, but are not limited to: M72, a fusion protein derived from the antigens Mtb32a and Mtb39; HyVac-1, a fusion protein derived from antigen 85b and ESAT-6; HyVac-4, a fusion protein derived from antigen 85b and Tb10.4; MVA85a, a modified vaccinia virus Ankara expressing antigen 85a; and Aeras-402, adenovirus 35 expressing a fusion protein derived from antigen 85a, antigen 85b and Tb10.4.

Abbreviations employed herein include the following:
ACN=acetonitrile; CBZ-Cl=benzyl chloroformate; DMSO=dimethyl sulfoxide; Et=ethyl;; EtOH=ethanol;

GFP=green fluorescent protein; HATU=(1-[Bis(dimethyl-amino)methylene]-1H-1,2,3-triazolo[4,5-b]pyridinium 3-oxid hexafluorophosphate), HET=heterocycle; H₂=hydrogen gas, HPLC=high-performance liquid chromatography; LC-MS=liquid chromatography/mass spectrometry; Me=methyl; MeOH=methanol; MIC=minimum inhibitory concentration; MW=molecular weight; MS=mass spectrometry; Mtb=Mycobacterium tuberculosis; prep=preparative; RT=room temperature; TB=tuberculosis; TEA=triethylamine; TFA=trifluoroacetic acid; THF=tetrahydrofuran; and TBDMS=tert-butyl dimethylsilyl.

Methods for Making the Compounds of Formula (I) and (II):

The Compounds of Formula (I) and (II) can be prepared according to the following reaction schemes and EXAMPLES, or modifications thereof, using readily available starting materials, reagents and conventional synthesis procedures. In these reactions, it is also possible to make use of variations which are themselves known to those of ordinary skill in this art, but are not mentioned in greater detail. Alternative synthetic pathways and analogous structures will be apparent to those skilled in the art of organic synthesis in light of the following reaction schemes and EXAMPLES.

General Procedure A

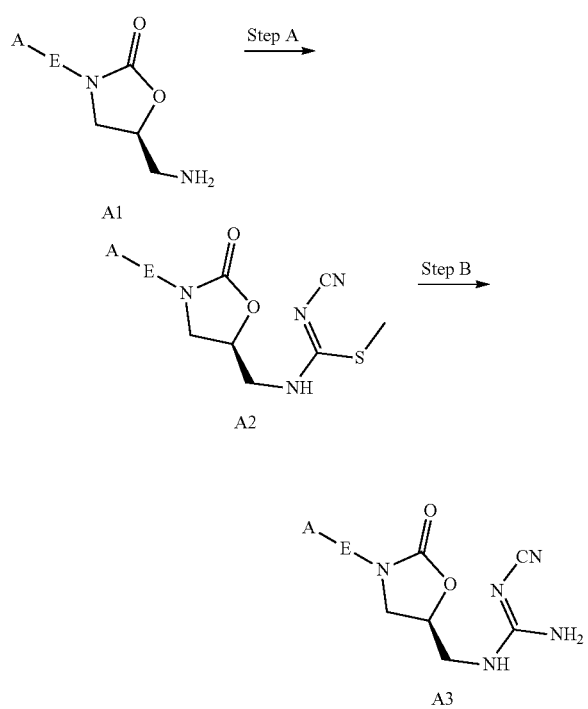

Step A: Dimethyl cyanocarbonimidodithioate is added to a solution of A1 in ethanol. The mixture is stirred at 80° C. for 16 h. The precipitate is collected by filtration and dried to give A2.

Step B: NH₃ in THF is added to a solution of A2 in ethanol. The mixture is stirred at 70° C. for 1 h. The mixture is concentrated to give A3.

EXAMPLE 1

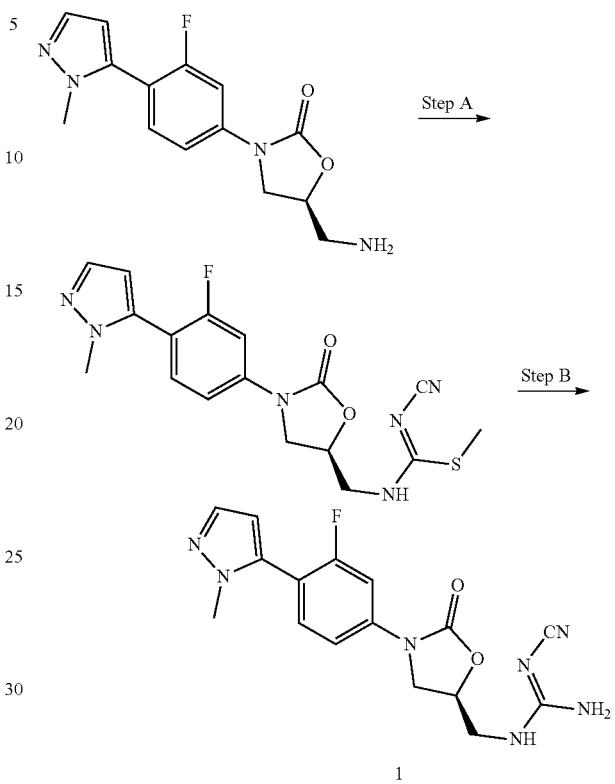

(S,E)-2-cyano-1-((3-(3-fluoro-4-(1-methyl-1H-pyrazol-5-yl)phenyl)-2-oxo oxazolidin-5-yl)methyl) -3-methylguanidine Step A: methyl (S,Z)-N'-cyano-N-((3-(3-fluoro-4-(1-methyl-1H-pyrazol-5-yl)phenyl) -2-oxooxazolidin-5-yl)methyl)carbamimidothioate Dimethyl cyanocarbonimidodithioate (176 mg, 1.21 mmol) was added to a solution of (S)-5-(aminomethyl)-3-(3-fluoro-4-(1-methyl-1H-pyrazol-5-yl)phenyl)oxazolidin-2-one (140 mg, 0.48 mmol) (synthesis described in PCT/US16/057257, hereby incorporated by reference) in ethanol (2 mL). Then the mixture was stirred at 80° C. for 16 h. The precipitate was collected by filtration and dried to give methyl (S,Z)-N'-cyano-N-((3-(3-fluoro-4-(1-methyl-1H-pyrazol-5-yl)phenyl)-2-oxooxazolidin-5-yl)methyl)carbamimidothioate (140 mg, 0.34 mmol). ¹H NMR (400 MHz, DMSO-d6) δ 8.67 (brs, 1H), 7.65 (dd, J=12.8, 2.0 Hz, 1H), 7.54-7.47 (m, 3H), 6.38 (d, J=1.2 Hz, 1H), 4.96-4.90 (m, 1H), 4.25-4.20 (m, 1H), 3.90-3.88 (m, 1H), 3.73 (s, 3H), 3.73-3.67 (m, 2H), 2.60 (s, 3H). MS (ESI) m/z 389.1 [M+H⁺].

Step B: (S,E)-2-cyano-1-((3-(3-fluoro-4-(1-methyl-1H-pyrazol-5-yl)phenyl)-2-oxo oxazolidin-5-yl) methyl)guanidine 1.0 mL NH₃ in THF(2 M, 2.0 mmol) was added to a solution of methyl (S,Z)-N'-cyano-N-((3-(3-fluoro-4-(1-methyl-1H-pyrazol-5-yl)phenyl)-2-oxooxazolidin-5-yl)

methyl)carbamimidothioate (70 mg, 0.18 mmol) in ethanol (2 mL). Then the mixture was stirred at 70° C. for 1 h. The mixture was concentrated to give crude product, and the residue was purified by prep-HPLC (Method TFA (Column: Waters XSELECT C18 150*30 mm*5 um; Condition: water (0.1% TFA)-ACN; Begin B: 14; End B: 44; Gradient Time (min): 10; 100% B Hold Time (min): 2; FlowRate (ml/min): 25)) to give (S,E)-2-cyano-1-((3-(3-fluoro-4-(1-methyl -1H-pyrazol-5-yl)phenyl)-2-oxooxazolidin-5-yl)methyl)guanidine (43 mg, 0.12 mmol). $^1$HNMR (400 MHz, DMSO-d6) δ 7.64 (dd, J=12.8, 2.0 Hz, 1H), 7.52-7.47 (m, 3H), 7.16 (brs, 1H), 6.84 (brs, 2H), 6.38 (d, J=1.2 Hz, 1H), 4.83-4.80 (m, 1H), 4.21-4.16 (m, 1H), 3.81-3.77 (m, 1H), 3.73 (s, 3H), 3.49-3.45 (m, 2H). MS (ESI) m/z 358.0 [M+H$^+$].

The following compounds were made using General Procedure A substituting the appropriate starting materials.

| Example | Structure | IUPAC Name | Mass M + H$^+$ |
|---|---|---|---|
| 1 | 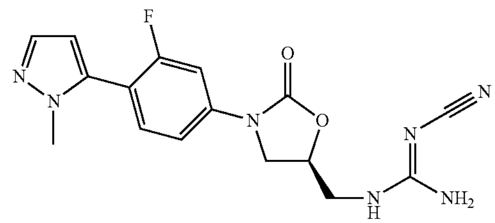 [SMILES: Cn1nccc1-c1ccc(N2C[C@H](CN/C(N)=N/C#N)OC2=O)cc1F] | (S,E)-2-cyano-1-((3-(3-fluoro-4-(1-methyl-1H-pyrazol-5-yl)phenyl)-2-oxooxazolidin-5-yl)methyl)guanidine | 358.0 |
| 2 | 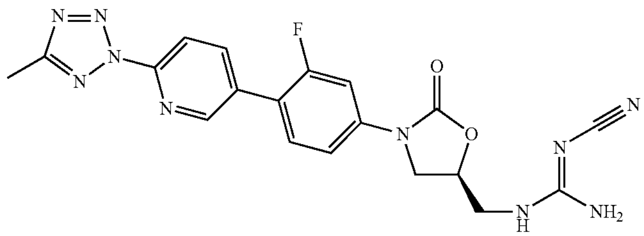 [SMILES: Cc1nnn(-c2ccc(-c3ccc(N4C[C@H](CN/C(N)=N/C#N)OC4=O)cc3F)cn2)n1] | (S,E)-2-cyano-1-((3-(3-fluoro-4-(6-(5-methyl-2H-tetrazol-2-yl)pyridin-3-yl)phenyl)-2-oxooxazolidin-5-yl)methyl)guanidine | 409.0 |
| 3 | 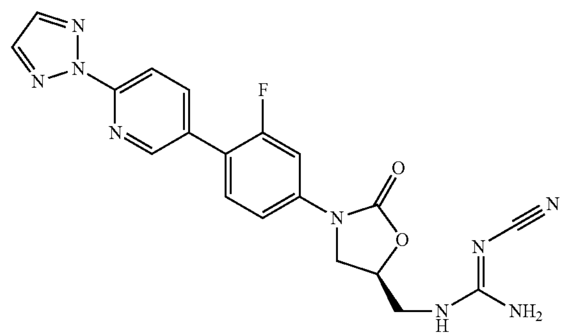 [SMILES: N#C/N=C(\N)NC[C@H]1CN(c2ccc(-c3ccc(-n4nccn4)nc3)c(F)c2)C(=O)O1] | (S,E)-1-((3-(4-(6-(2H-1,2,3-triazol-2-yl)pyridin-3-yl)-3-fluorophenyl)-2-oxooxazolidin-5-yl)methyl)-2-cyanoguanidine | 422.0 |
| 4 | 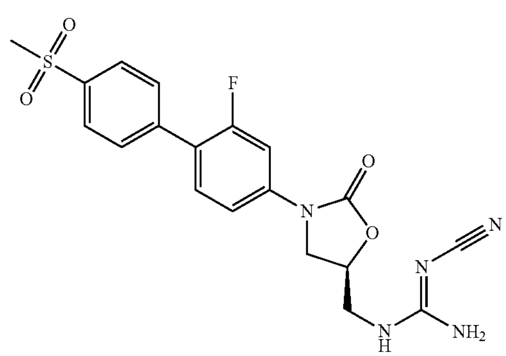 [SMILES: CS(=O)(=O)c1ccc(-c2ccc(N3C[C@H](CN/C(N)=N/C#N)OC3=O)cc2F)cc1] | (S,E)-2-cyano-1-((3-(2-fluoro-4'-(methylsulfonyl)-[1,1'-biphenyl]-4-yl)-2-oxooxazolidin-5-yl)methyl)guanidine | 432.0 |

| Example | Structure | IUPAC Name | Mass M + H⁺ |
|---|---|---|---|
| 5 | 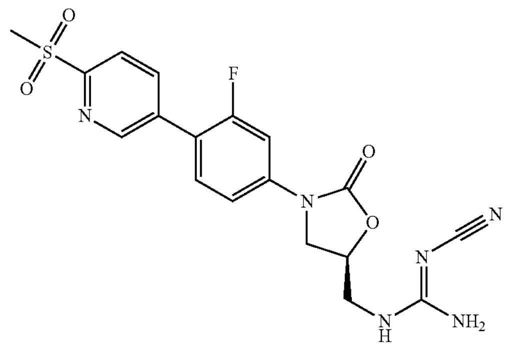 [SMILES: CS(=O)(=O)c1ccc(-c2ccc(N3C[C@H](CN/C(N)=N/C#N)OC3=O)cc2F)cn1] | (S,E)-2-cyano-1-((3-(3-fluoro-4-(6-(methylsulfonyl)pyridin-3-yl)phenyl)-2-oxooxazolidin-5-yl)methyl)guanidine | 432.9 |

General Procedure B

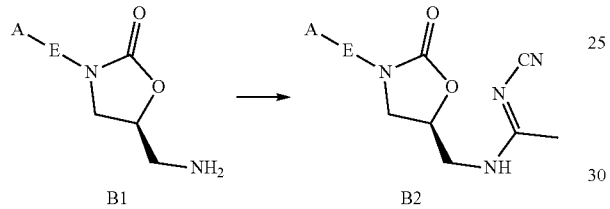

(E)-methyl N-cyanoacetimidate is added to a solution of B1 in MeOH. The mixture is stirred at 20° C. for 1 h or until LCMS shows the reaction is complete. The mixture is purified by prep-HPLC to give B2.

EXAMPLE 6

(S,E)-N'-cyano-N-((3-(3-fluoro-4-(1-methyl-1H-pyrazol-5-yl)phenyl)-2-oxooxazolidin-5-yl)methyl)acetimidamide (E)-methyl N-cyanoacetimidate (47 mg, 0.48 mmol) was added to a solution of (S)-5-(aminomethyl) -3-(3-fluoro-4-(1-methyl-1H-pyrazol-5-yl)phenyl) oxazolidin-2-one (70 mg, 0.24 mmol) (synthesis described in PCT/US16/057257, hereby incorporated by reference) in MeOH (1 mL). The mixture was stirred at 20° C. for 1 h (LCMS showed the reaction was completed). The mixture was purified by prep-HPLC (Method Neutral (Column: Xtimate C18 150*25 mm*5 um; Condition: water (10 mM NH₄HCO₃)-ACN; Begin B: 26; End B: 56; Gradient Time (min): 10; 100% B Hold Time (min): 2; FlowRate (ml/min): 25)) to give (S,E)-N'-cyano-N-((3 -(3-fluoro-4-(1-methyl-1H-pyrazol-5-yl)phenyl)-2-oxooxazolidin-5-yl)methyl)acetimidamide (52 mg, 0.14 mmol). $^1$H NMR (400 MHz, DMSO-d6) δ 9.18 (brs, 1H), 7.65 (dd, J=12.8, 2.0 Hz, 1H), 7.55-7.50 (m, 2H), 7.46-7.45 (m, 1H), 6.38 (s, 1H), 4.89-4.86 (m, 1H), 4.23-4.18 (m, 1H), 3.83-3.80 (m, 1H), 3.72 (s, 3H), 3.61-3.59 (m, 2H), 2.24 (s, 3H). MS (ESI) m/z: 357.0 [M+H⁺].

The following compounds were made using General Procedure B substituting the appropriate starting materials.

| Example No. | Structure | IUPAC Name | M + H⁺ |
|---|---|---|---|
| 6 | 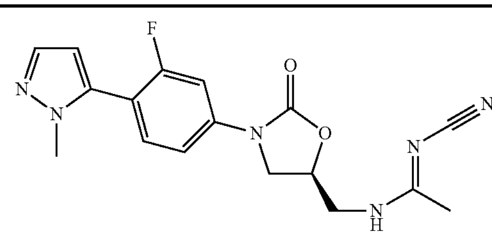 | (S,E)-N'-cyano-N-((3-(3-fluoro-4-(1-methyl-1H-pyrazol-5-yl)phenyl)-2-oxooxazolidin-5-yl)methyl)acetimidamide | 357.0 |

| Example No. | Structure | IUPAC Name | M + H⁺ |
|---|---|---|---|
| 7 | 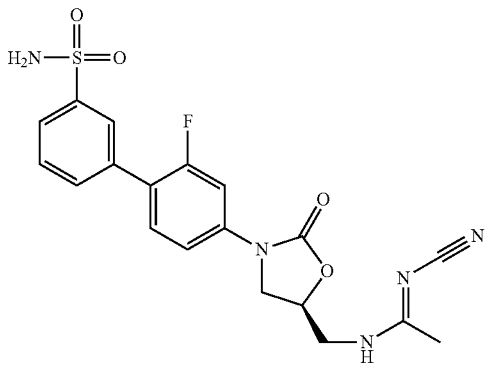 [SMILES: C/C(=N\C#N)NC[C@H]1CN(c2ccc(-c3cccc(S(N)(=O)=O)c3)c(F)c2)C(=O)O1] | (S,E)-N'-cyano-N-((3-(2-fluoro-3'-sulfamoyl-[1,1'-biphenyl]-4-yl)-2-oxooxazolidin-5-yl)methyl)acetimidamide | 432.0 |
| 8 | 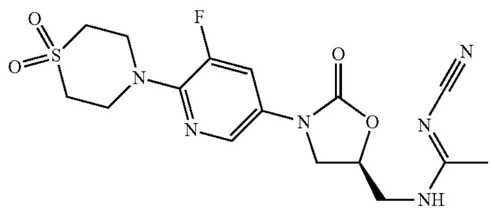 [SMILES: C/C(=N\C#N)NC[C@H]1CN(c2cnc(N3CCS(=O)(=O)CC3)c(F)c2)C(=O)O1] | (S,E)-N'-cyano-N-((3-(6-(1,1-dioxidothiomorpholino)-5-fluoropyridin-3-yl)-2-oxooxazolidin-5-yl)methyl)acetimidamide | 411.0 |
| 9 | 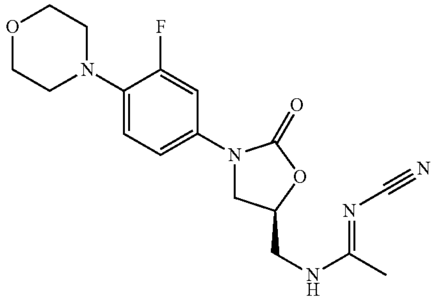 [SMILES: C/C(=N\C#N)NC[C@H]1CN(c2ccc(N3CCOCC3)c(F)c2)C(=O)O1] | (S,E)-N'-cyano-N-((3-(3-fluoro-4-morpholinophenyl)-2-oxooxazolidin-5-yl)methyl)acetimidamide | 362.0 |
| 10 | 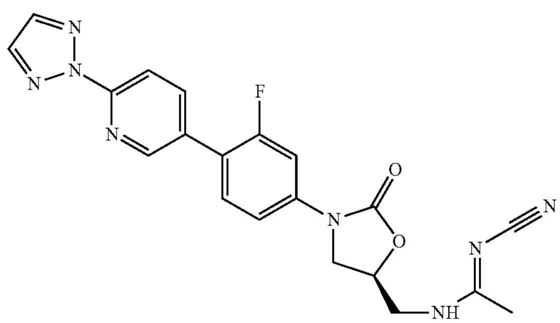 [SMILES: C/C(=N\C#N)NC[C@H]1CN(c2ccc(-c3ccc(-n4nccn4)nc3)c(F)c2)C(=O)O1] | (S,E)-N-((3-(4-(6-(2H-1,2,3-triazol-2-yl)pyridin-3-yl)-3-fluorophenyl)-2-oxooxazolidin-5-yl)methyl)-N'-cyanoacetimidamide | 421.1 |
| 11 | 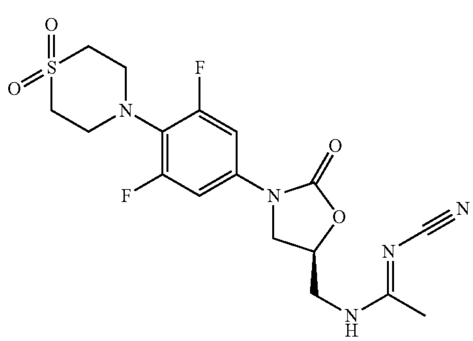 [SMILES: C/C(=N\C#N)NC[C@H]1CN(c2cc(F)c(N3CCS(=O)(=O)CC3)c(F)c2)C(=O)O1] | (S,E)-N'-cyano-N-((3-(4-(1,1-dioxidothiomorpholino)-3,5-difluorophenyl)-2-oxooxazolidin-5-yl)methyl)acetimidamide | 428.0 |

| Example No. | Structure | IUPAC Name | M + H⁺ |
|---|---|---|---|
| 12 | 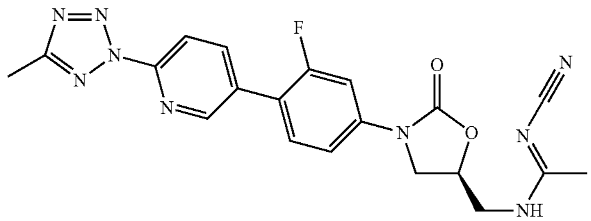 [SMILES: C/C(=N\C#N)NC[C@H]1CN(c2ccc(-c3ccc(-n4nnc(C)n4)nc3)c(F)c2)C(=O)O1] | (S,E)-N'-cyano-N-((3-(3-fluoro-4-(6-(5-methyl-2H-tetrazol-2-yl)pyridin-3-yl)phenyl)-2-oxooxazolidin-5-yl)methyl)acetimidamide | 408.0 |
| 13 | 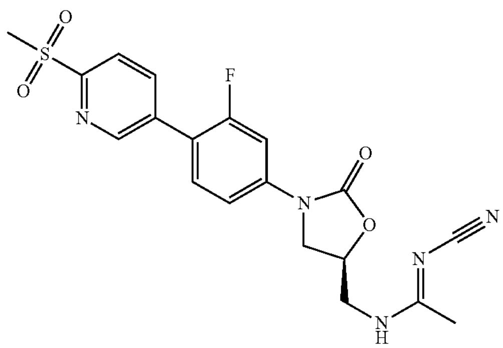 [SMILES: C/C(=N\C#N)NC[C@H]1CN(c2ccc(-c3ccc(S(C)(=O)=O)nc3)c(F)c2)C(=O)O1] | (S,E)-N'-cyano-N-((3-(3-fluoro-4-(6-(methylsulfonyl)pyridin-3-yl)phenyl)-2-oxooxazolidin-5-yl)methyl)acetimidamide | 431.9 |
| 14 | 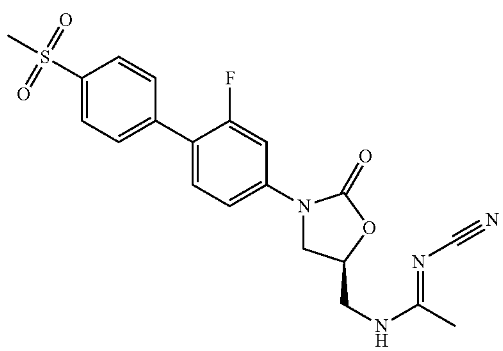 [SMILES: C/C(=N\C#N)NC[C@H]1CN(c2ccc(-c3ccc(S(C)(=O)=O)cc3)c(F)c2)C(=O)O1] | (S,E)-N'-cyano-N-((3-(2-fluoro-4'-(methylsulfonyl)-[1,1'-biphenyl]-4-yl)-2-oxooxazolidin-5-yl)methyl)acetimidamide | 431.0 |

General Procedure C

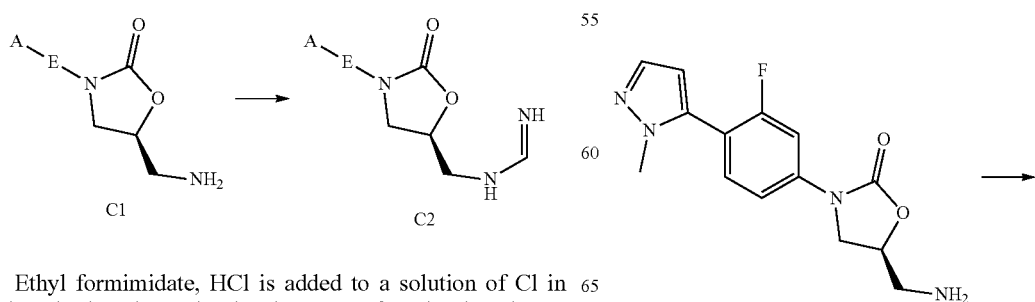

Ethyl formimidate, HCl is added to a solution of C1 in ethanol. The mixture is stirred at 80° C. for 2 h. The mixture is concentrated to give C2 which is purified by prep-HPLC.

EXAMPLE 15

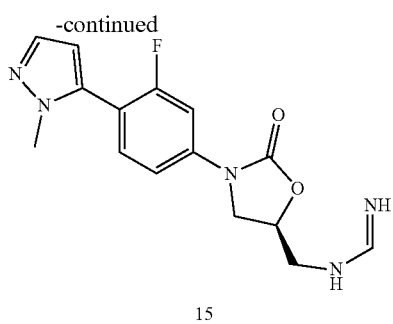

Synthesis of (S)-N-((3-(3-fluoro-4-(1-methyl-1H-pyrazol-5-yl)phenyl)-2-oxooxazolidin-5-yl)methyl)formimidamide Ethyl formimidate, HCl (66 mg, 0.60 mmol) was added to a solution of (S)-5-(aminomethyl) -3-(3-fluoro-4-(1-methyl-1H-pyrazol-5-yl)phenyl) oxazolidin-2-one (70 mg, 0.24 mmol) (synthesis described in PCT/US16/057257, hereby incorporated by reference) in ethanol (1 mL). The mixture was stirred at 80° C. for 2 h. The mixture was concentrated to give a crude, the residue was purified by prep-HPLC (Method TFA, see Example 1) to give (S)-N-((3-(3-fluoro-4-(1-methyl-1H-pyrazol-5-yl)phenyl)-2-oxooxazolidin-5-yl)methyl)formimidamide (37 mg, 0.11 mmol). $^1$H NMR (400 MHz, CD$_3$OD) δ 8.09-8.00 (m, 2H), 7.82 (dd, J=12.8, 2.0 Hz, 1H), 7.60-7.56 (m, 2H), 6.74 (d, J=2.4 Hz, 1H), 5.04-5.00 (m, 1H), 4.38-4.32 (m, 1H), 3.97-3.93 (m, 1H), 3.95 (s, 3H), 3.85-3.849 (m, 1H), 3.80-3.77 (m, 1H). MS (ESI) m/z 318.0 [M+H$^+$].

The following compounds were made using General Procedure C substituting the appropriate starting materials.

| Example No. | Structure | IUPAC Name | Mass M + H$^+$ |
|---|---|---|---|
| 15 | 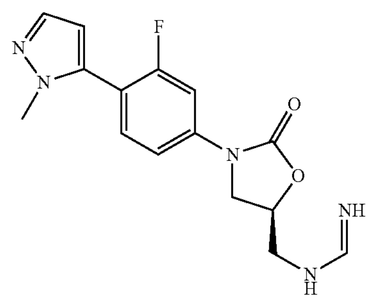 [SMILES: Cn1nccc1-c1ccc(N2C[C@H](CNC=N)OC2=O)cc1F] | (S)-N-((3-(3-fluoro-4-(1-methyl-1H-pyrazol-5-yl)phenyl)-2-oxooxazolidin-5-yl)methyl)formimidamide | 318.0 |
| 16 | 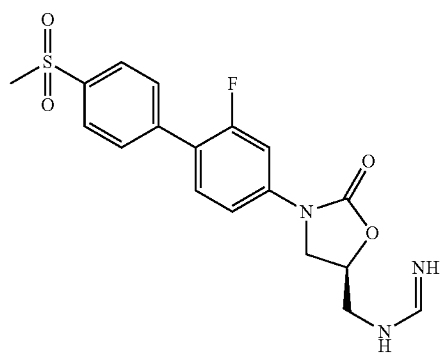 [SMILES: CS(=O)(=O)c1ccc(-c2ccc(N3C[C@H](CNC=N)OC3=O)cc2F)cc1] | (S)-N-((3-(2-fluoro-4'-(methylsulfonyl)-[1,1'-biphenyl]-4-yl)-2-oxooxazolidin-5-yl)methyl)formimidamide | 392.0 |
| 17 | 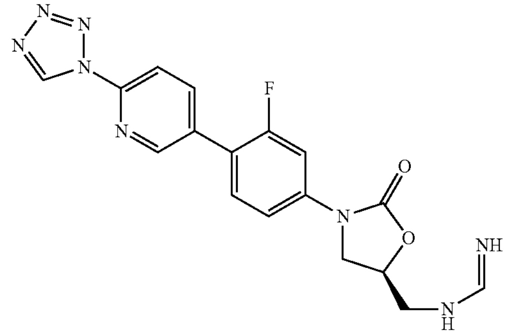 [SMILES: N=CNC[C@H]1CN(c2ccc(-c3ccc(-n4cnnn4)nc3)c(F)c2)C(=O)O1] | (S)-N-((3-(4-(6-(1H-tetrazol-1-yl)pyridin-3-yl)-3-fluorophenyl)-2-oxooxazolidin-5-yl)methyl)formimidamide | 383.0 |

-continued

| Example No. | Structure | IUPAC Name | Mass M + H+ |
|---|---|---|---|
| 18 | 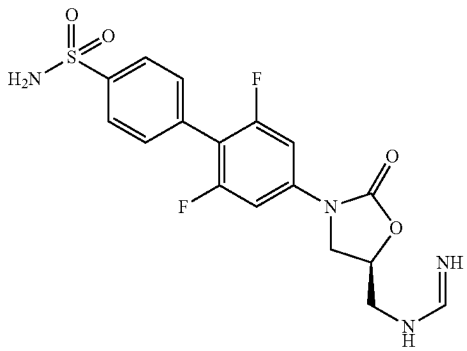 [SMILES: N=CNC[C@H]1CN(c2cc(F)c(-c3ccc(S(N)(=O)=O)cc3)c(F)c2)C(=O)O1] | (S)-N-((3-(2,6-difluoro-4'-sulfamoyl-[1,1'-biphenyl]-4-yl)-2-oxooxazolidin-5-yl)methyl)formimidamide | 411.0 |
| 19 | 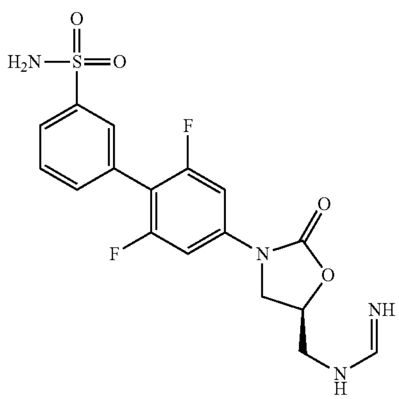 [SMILES: N=CNC[C@H]1CN(c2cc(F)c(-c3cccc(S(N)(=O)=O)c3)c(F)c2)C(=O)O1] | (S)-N-((3-(2,6-difluoro-3'-sulfamoyl-[1,1'-biphenyl]-4-yl)-2-oxooxazolidin-5-yl)methyl)formimidamide | 410.9 |
| 20 | 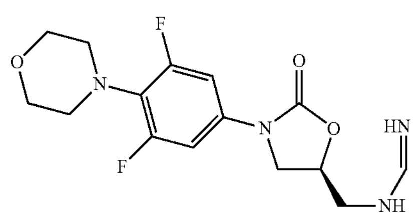 [SMILES: N=CNC[C@H]1CN(c2cc(F)c(N3CCOCC3)c(F)c2)C(=O)O1] | (S)-N-((3-(3,5-difluoro-4-morpholinophenyl)-2-oxooxazolidin-5-yl)methyl)formimidamide | 341.0 |

General Procedure D

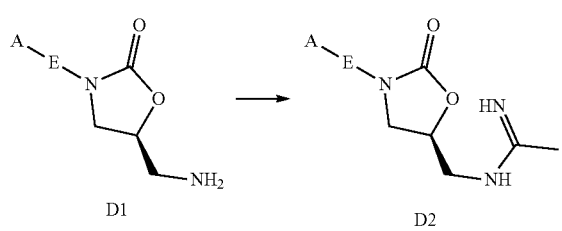

Ethyl acetimidate is added to a solution of D1 in ethanol. The mixture is stirred at 35° C. for 14 h. The mixture can be purified by prep-HPLC to give D2.

EXAMPLE 21

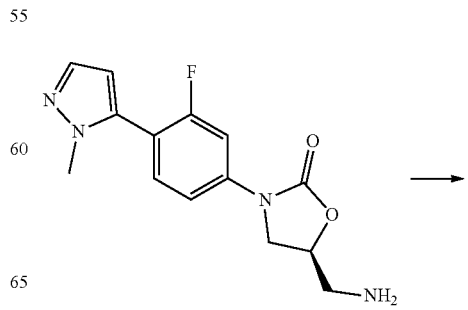

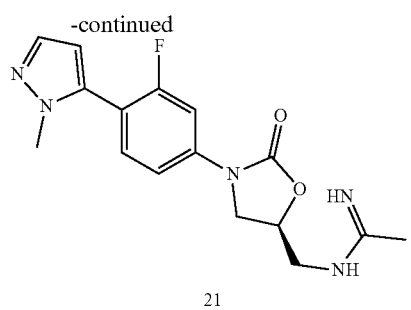

21

Synthesis of (S)-N-((3-(3-fluoro-4-(1-methyl-1H-pyrazol-5-yl)phenyl)-2-oxooxazolidin-5-yl)methyl)acetimidamide Ethyl acetimidate (63 mg, 0.72 mmol) was added to a solution of (S)-5-(aminomethyl)-3-(3-fluoro-4-(1-methyl-1H-pyrazol-5-yl)phenyl)oxazolidin-2-one (70 mg, 0.24 mmol) (synthesis described in PCT/US16/057257, hereby incorporated by reference) in EtOH (1.5 mL). The mixture was stirred at 35° C. for 14 h. The mixture was purified by prep-HPLC (Method TFA) to give (S)-N-((3-(3-fluoro-4-(1-methyl-1H-pyrazol-5-yl)phenyl)-2-oxooxazolidin -5-yl)methyl)acetimidamide (55 mg, 0.16 mmol, 68% yield). $^1$1-1NMR (400 MHz, DMSO-d6) δ 9.74 (brs, 1H), 9.29 (brs, 1H), 8.85 (brs, 1H), 7.67 (dd, J=12.8, 2.0 Hz, 1H), 7.55-7.49 (m, 3H), 6.38 (d, J=1.2 Hz, 1H), 4.92-4.87 (m, 1H), 4.26-4.21 (m, 1H), 3.82-3.80 (m, 1H), 3.78 (s, 3H), 3.73-3.66 (m, 2H), 2.19 (s, 3H). MS (ESI) m/z 332.0 [M+H$^+$].

The following compounds were made using General Procedure D substituting the appropriate starting materials.

| Examples | Structure | IUPAC Name | Observed Mass M + H$^+$ |
|---|---|---|---|
| 21 | 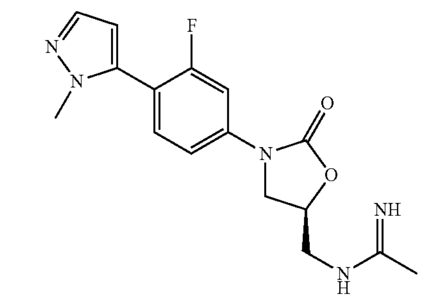 [SMILES: CC(=N)NC[C@H]1CN(c2ccc(-c3ccnn3C)c(F)c2)C(=O)O1] | (S)-N-((3-(3-fluoro-4-(1-methyl-1H-pyrazol-5-yl)phenyl)-2-oxooxazolidin-5-yl)methyl)acetimidamide | 332.0 |
| 22 | 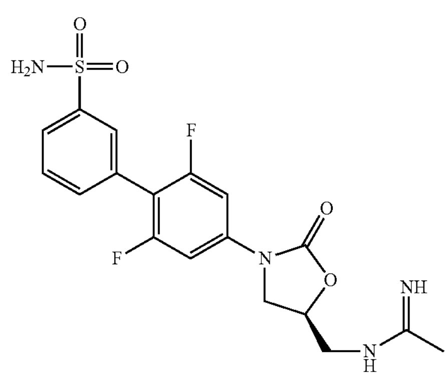 [SMILES: CC(=N)NC[C@H]1CN(c2cc(F)c(-c3cccc(S(N)(=O)=O)c3)c(F)c2)C(=O)O1] | (S)-N-((3-(2,6-difluoro-3'-sulfamoyl-[1,1'-biphenyl]-4-yl)-2-oxooxazolidin-5-yl)methyl)acetimidamide | 425.0 |
| 23 | 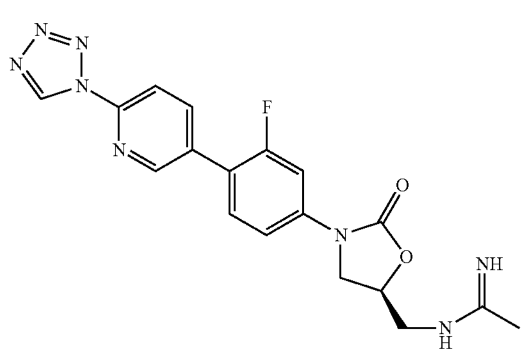 [SMILES: CC(=N)NC[C@H]1CN(c2ccc(-c3ccc(-n4cnnn4)nc3)c(F)c2)C(=O)O1] | (S)-N-((3-(4-(6-(1H-tetrazol-1-yl)pyridin-3-yl)-3-fluorophenyl)-2-oxooxazolidin-5-yl)methyl)acetimidamide | 397.0 |

| Examples | Structure | IUPAC Name | Observed Mass M + H+ |
|---|---|---|---|
| 24 | 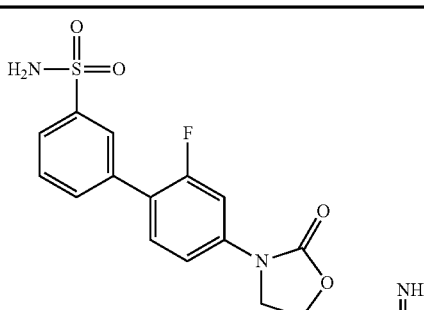 | (S)-N-((3-(2-fluoro-3'-sulfamoyl-[1,1'-biphenyl]-4-yl)-2-oxooxazolidin-5-yl)methyl)acetimidamide | 407.0 |

Biological Assays

*Mycobacterium Tuberculosis* (Mtb) Growth Assay

Inhibition of *Mycobacterium tuberculosis* (Ntb) growth was assessed on two in vivo-relevant carbon sources, glucose (Glu) and cholesterol (Cho), at pH 6.8. For glucose as a carbon source, the media consisted of Middlebrook 7H9 broth supplemented with 4 g/L glucose, 0.08 g/L NaCl, 5 g/L BSA fraction V and 0.05% tyloxapol. For cholesterol as a carbon source, the media consisted of Middlebrook 7H9 broth supplemented with 97mg/L cholesterol, 0.08 g/L NaCl, 5 g/L BSA fraction V and 0.05% tyloxapol. Mtb expressing green fluorescent protein (Mtb-GFP; H37Rv pMSP12::GFP) was pre-adapted to growth on the relevant carbon source in Middlebrook 7H9-broth base supplemented with bovine serum albumin and tyloxapol prior to the screen. Bacteria were dispensed into 384-well microtiter plates at approximately 2×10$^4$ actively growing cells in 24 µL volumes per well. Microtiter plates were pre-dispensed with 0.2 µL compound, dimethylsulfoxide (negative control) or rifampicin (25 µM; positive control). Cells were exposed to 2-fold serial dilutions of compounds from 50 µM to 0.049 µM. In some experiments, compounds were tested at lower concentrations. Growth inhibition was assessed after a 7-day growth period by measuring fluorescence using a spectrophotometer. In negative control wells, cells were still actively growing at the time of readout. The lowest concentration of test compound required to inhibit 95% of the growth of the bacteria was defined as the MITC95. All studies were done in a BSL3 facility.

| Example | Mtb Cho MITC95_µM | Mtb Glu MITC95_µM |
|---|---|---|
| 1 | 0.78 | 0.78 |
| 2 | 0.19 | 0.09 |
| 3 | 0.19 | 0.19 |
| 4 | 0.39 | 0.39 |
| 5 | 0.39 | 0.78 |
| 6 | 0.78 | 0.78 |
| 7 | 1.14 | 1.50 |
| 8 | 6.25 | 6.25 |
| 9 | 3.12 | 3.12 |
| 10 | 0.39 | 0.14 |
| 11 | 3.12 | 1.50 |
| 12 | 0.19 | 0.14 |
| 13 | 1.50 | 0.78 |
| 14 | 0.58 | 0.58 |
| 15 | 0.78 | 0.39 |
| 16 | 0.39 | 0.19 |
| 17 | 0.24 | 0.12 |
| 18 | 0.39 | 0.29 |
| 19 | 0.68 | 0.39 |
| 20 | 0.58 | 0.14 |
| 21 | 25 | 25 |
| 22 | 6.25 | 3.12 |
| 23 | 12.5 | 6.25 |
| 24 | 6.25 | 6.25 |
| Linezolid | 3.14 | 4.58 |

What is claimed is:

1. A compound of Formula I, or a pharmaceutically acceptable salt thereof:

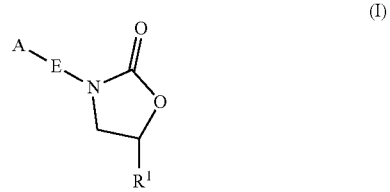

(I)

wherein:
R$^1$ is —CH$_2$NHC(R$^2$)NR$^3$;
R$^2$ is H, C$_1$-C$_6$ alkyl, or NR$^4$R$^5$;
R$^3$ is H, C$_1$-C$_6$ alkyl, or CN;
R$^4$ is H or C$_1$-C$_6$ alkyl;
R$^5$ is H or C$_1$-C$_6$ alkyl;
E is phenyl or pyridyl, wherein the phenyl and pyridyl are substituted with one or two fluorines;
A is

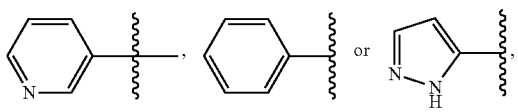

wherein A is substituted with up to four substituents, which are independently selected from halogen, $C_1$-$C_6$ alkyl, —CN, $C_1$-$C_6$ haloalkyl, —$SO^2C_1$-$C_6$ alkyl, —$SO^2NR^4R^5$, $C_1$-$C_6$ alkoxy, $C_1$-$C_6$ haloalkoxy, —OH, oxo, tetrazole, triazole, and $C_3$-$C_6$ cycloalkyl, and wherein the tetrazole, triazole, and $C_3$-$C_6$ cycloalkyl are unsubstituted or substituted with up to three substituents selected from C1-C6 alkyl.

2. The compound of claim 1, or a pharmaceutically acceptable salt thereof, wherein $R^2$ is $NH_2$.
3. The compound of claim 1, or a pharmaceutically acceptable salt thereof, wherein $R^2$ is hydrogen.
4. The compound of claim 1, or a pharmaceutically acceptable salt thereof, wherein $R^2$ is methyl.
5. The compound of claim 1, or a pharmaceutically acceptable salt thereof, wherein $R^3$ is —CN.
6. The compound of claim 1, or a pharmaceutically acceptable salt thereof, wherein $R^3$ is hydrogen.
7. The compound of claim 1, or a pharmaceutically acceptable salt thereof, wherein A is:

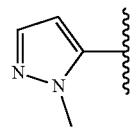

or phenyl, wherein the phenyl is substituted with one substituent independently selected from —$SO^2CH_3$ or —$SO^2NH^2$; or pyridyl, wherein the pyridyl is substituted with one substituent independently selected from —$SO^2CH_3$, 1H-tetrazol-1-yl, 5-m ethyl-2H-tetrazol-2-yl, 2H-1,2,3-triazol-2-yl.

8. A compound, or pharmaceutically acceptable salt thereof, selected from:

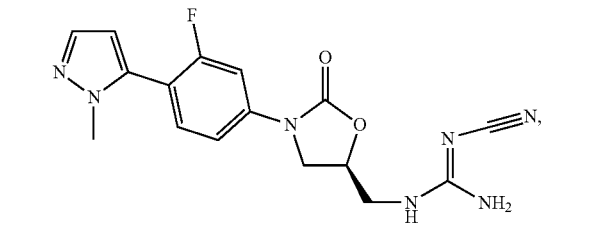

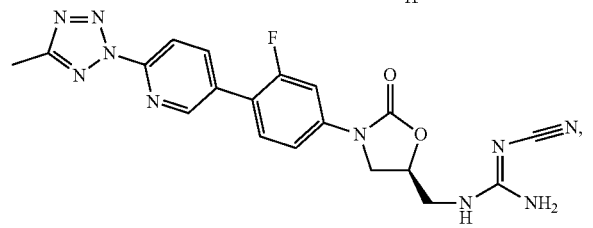

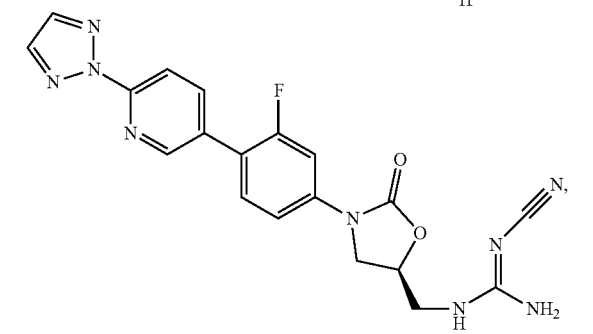

-continued

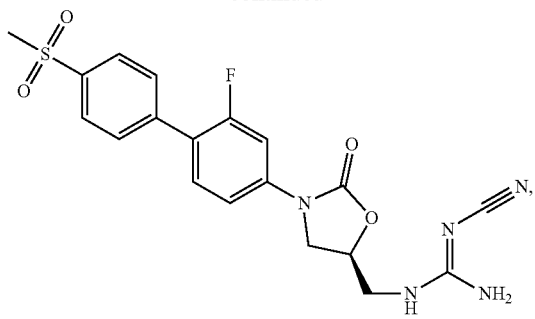

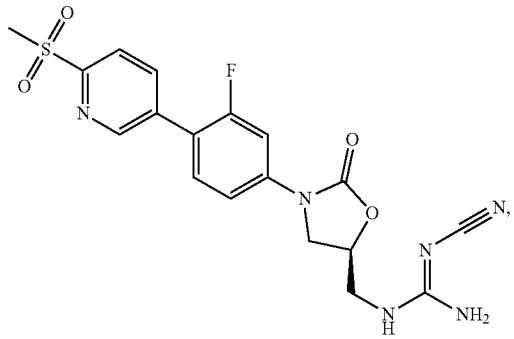

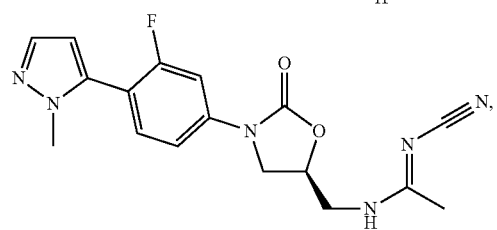

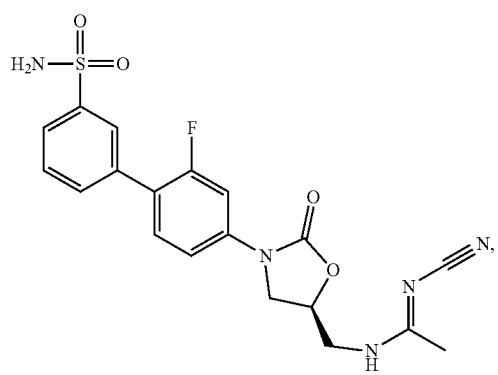

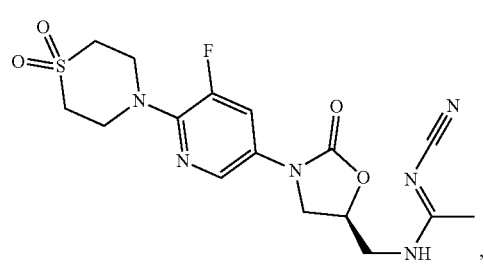

-continued
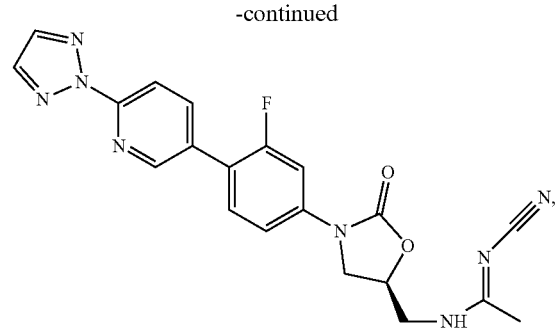
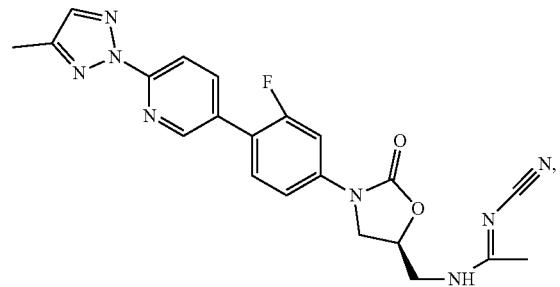
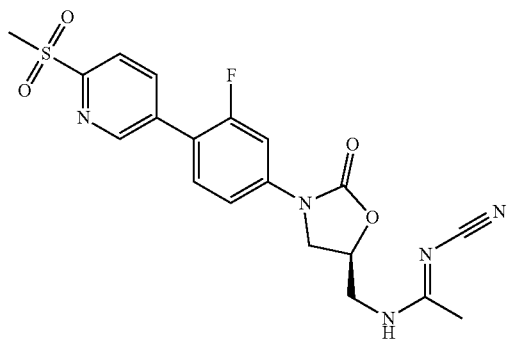
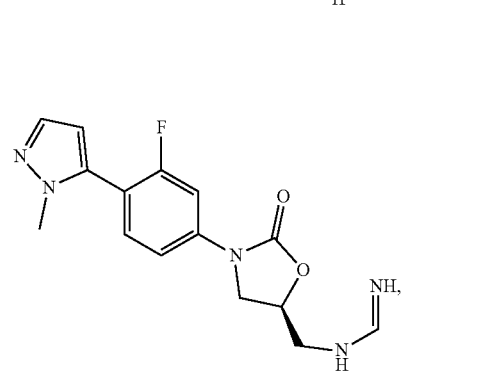
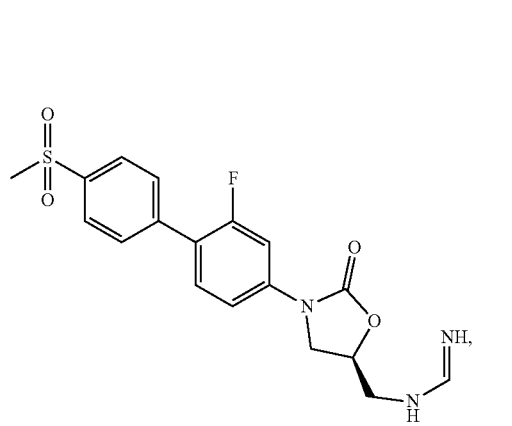
-continued
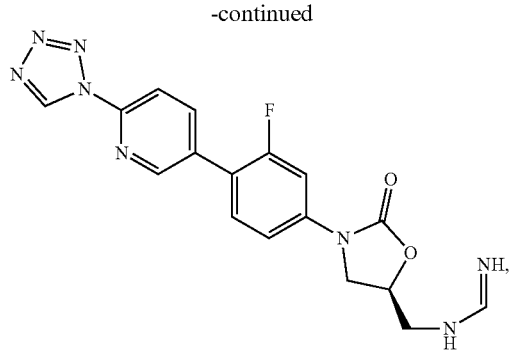
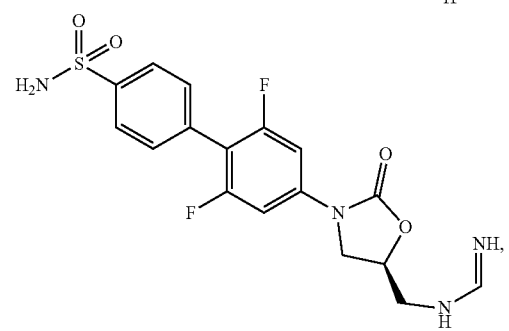
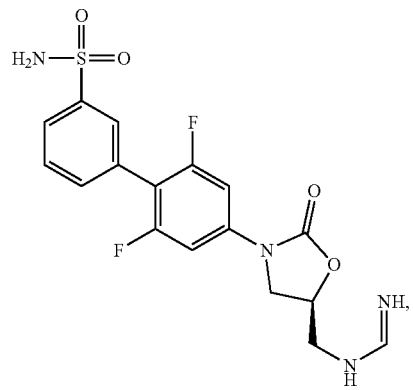
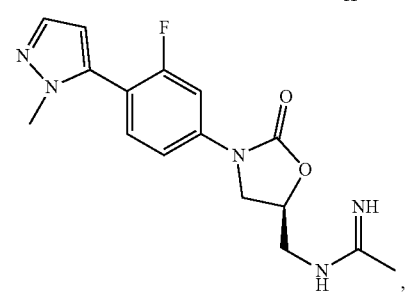
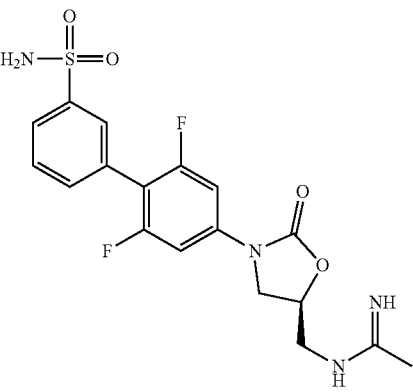

-continued

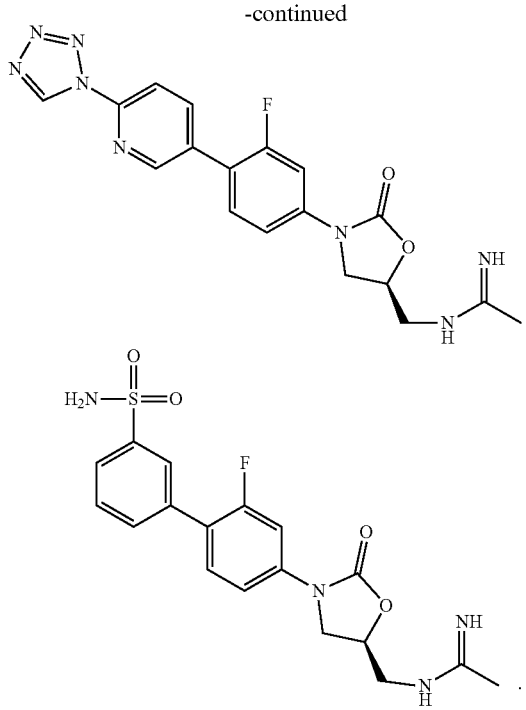

and

9. A pharmaceutical composition which comprises a therapeutically effective amount of a compound according to claim 1, or a pharmaceutically acceptable salt thereof, and a pharmaceutically acceptable carrier.

10. A method for treating a bacterial infection which comprises administering to a subject having said mycobacterial infecttion a therapeuticallu effective amount of a compound according to claim 1, or a pharmaceutically acceptable salt thereof.

11. The method of claim 10, wherein the mycobacterial infection is due to *Mycobacterium tuberculosis*.

12. The method of claim 10, wherein the mycobacterial infection is due to *Nontuberculous mycobacteria* (NTM).

13. The method according to claim 10, wherein the compound or the pharmaceutically acceptable salt thereof is administered orally, parentally, or topically.

14. The method according to claim 11, wherein the *M. tuberculosis* is a drug resistant mycobacterial strain.

15. The method according to any of claim 11, further comprising the step of administering a second therapeutic agent for treating *M. tuberculosis*.

16. The method of claim 15, wherein the second therapeutic agent is selected from the group consisting of: ethambutol, pyrazinamide, isoniazid, levofloxacin, moxifloxacin, gatifloxacin, ofloxacin, kanamycin, amikacin, capreomycin, streptomycin, ethionamide, prothionamide, cycloserine, terididone, para-aminosalicylic acid, clofazimine, clarithromycin, amoxicillin-clavulanate, thiacetazone, meropenem-clavulanate, thioridazine, bedaquiline, ciprofloxacin, enviomycin, meropenem-clavulanate, rifabutin, and viomycin.

* * * * *